(12) United States Patent
Lakshman et al.

(10) Patent No.: US 8,501,931 B2
(45) Date of Patent: Aug. 6, 2013

(54) CONVERTIBLE NUCLEOSIDE DERIVATIVES

(75) Inventors: Mahesh K. Lakshman, Teaneck, NJ (US); Suyeal Bae, Seoul (KR)

(73) Assignee: Research Foundation of the City University of New York, New York, NY (US)

( * ) Notice: Subject to any disclaimer, the term of this patent is extended or adjusted under 35 U.S.C. 154(b) by 824 days.

(21) Appl. No.: 12/444,873

(22) PCT Filed: Oct. 12, 2007

(86) PCT No.: PCT/US2007/021808
§ 371 (c)(1),
(2), (4) Date: Mar. 5, 2010

(87) PCT Pub. No.: WO2008/045535
PCT Pub. Date: Apr. 17, 2008

(65) Prior Publication Data
US 2010/0179312 A1    Jul. 15, 2010

Related U.S. Application Data

(60) Provisional application No. 60/895,761, filed on Mar. 20, 2007, provisional application No. 60/829,168, filed on Oct. 12, 2006.

(51) Int. Cl.
*C07H 19/04* (2006.01)
*C07H 19/20* (2006.01)
*C07H 19/10* (2006.01)
*C07H 19/167* (2006.01)
*C07H 19/00* (2006.01)

(52) U.S. Cl.
USPC ....... 536/26.6; 536/26.7; 536/26.8; 536/27.8; 536/28.54

(58) Field of Classification Search
None
See application file for complete search history.

(56) References Cited

U.S. PATENT DOCUMENTS

| | | | |
|---|---|---|---|
| 4,916,218 | A | 4/1990 | Almond et al. |
| 5,705,621 | A | 1/1998 | Ravikumar |
| 6,166,198 | A | 12/2000 | Livingston |
| 2002/0107398 | A1 | 8/2002 | Assmann et al. |
| 2006/0165655 | A1 | 7/2006 | Babu et al. |

OTHER PUBLICATIONS

Lakshman et al., "Palladium-Catalyzed C-N Bond Formation: Facile and General Synthesis of N6-Aryl-2'-deoxyadenosine Analogues," J. Amer. Chem. Soc., 121(25), 6090-6091 (Jun. 10, 1999).*
Bae et al., "O6-(Benzotriazol-1-yl)inosine Derivatives: Easily Synthesized, Reactive Nucleosides," J. Amer. Chem. Soc., 129(4), 782-789 (Jan. 9, 2007).*
Bae et al., "A Novel Polymer Supported Approach to Nucleoside Modification," Journal of Organic Chemistry, 73(10), 3707-3713 (Apr. 23, 2008).*
Reese et al., "Reaction Between Nucleoside Base Residues and the Phosphorylating Agent Derived From 1-Hydroxybenzotriazole and 2-Chlorophenylphosphorodichloridate," Tetrahedron Letters, 26(18), 2245-2248 (1985).*
U.S. Statutory Invention Registration No. H1729 to Biller et al., published May 5, 1998 for "Method for Preparing Compounds Employing Solid Phase Synthesis and Novel Linker-Resin".
Wan, Zhao-Kui et al. A Highly Facile and Efficient One-Step Synthesis of N6-Adenosine and N6-2•-Deoxyadenosine Derivatives. Organic Letters 2005 vol. 7, No. 26 pp. 5877-5880.
Wan, Zhao-Kui et al. An Efficient Direct Amination of Cyclic Amides and Cyclic Ureas. Organic Letters 2006 vol. 8, No. 11 pp. 2425-2428.
Lin, Xiaoyu and Robins. Mild and Efficient Functionalization at C6 of Purine 2•-Deoxynucleosides and Ribonucleosides. Organic Letters 2000 vol. 2, No. 22 pp. 3497-3499.
Ferentz, A. E. and Verdine. Aminolysis of 2•-Deoxyinosine Aryl Ethers: Nucleoside Model Studies for the Synthesis of Functionally Tethered Oligonucleotides. Nucleosides & Nucleotides vol. 11, No. 10 1992 pp. 1749-1763.
Maruenda et al. Synthesis of 1,N6-Ethano-2•-deoxyadenosine, a Metabolic Product of 1,3-Bis(2-chloroethyl)nitrosourea, and its Incorporation into Oligomeric DNA. J. Org. Chem. 1998, 63, pp. 4385-4389.

(Continued)

*Primary Examiner* — Lawrence E Crane
(74) *Attorney, Agent, or Firm* — Hoffmann & Baron, LLP

(57) ABSTRACT

The present invention is directed to convertible nucleosides and polymer supported convertible nucleosides for use in $S_NAr$ displacement reactions. The convertible nucleosides can be used to synthesize numerous substituted purine and pyrimidine derivatives. An example of a polymer supported convertible nucleoside of the invention is

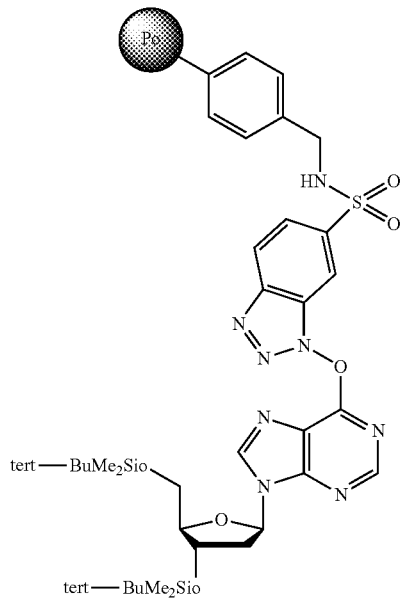

23 Claims, No Drawings

OTHER PUBLICATIONS

Gao et al. 6-O-(Pentafluorophenyl)-2•-deoxyguanosine: A Versatile synthon for Nucleoside and Oligonucleotide Synthesis. J. Org. Chem. 1992, 57, pp. 6954-6959.

Hofmann et al. Synthesis of oligodeoxynucleotides containing 6-N-([13C]methyl)adenine and 2-N-([13C]methyl)guanine. J. Chem. Soc., Perkin Trans. 1, 1997, pp. 1825-1828.

Fathi et al. Synthesis of 6-Substituted 2•-Deoxyguanosine Derivatives Using Trifluoroacetic Anhydride in Pyridine. Tetrahedron Letters, vol. 31, No. 3, pp. 319-322 1990.

Zemlicka and Endo. O6-(4-Nitrophenyl)inoside and -Guanosine as Chromogenic Substrates for Adenosine Deaminase. Nucleosides & Nucleotides, 15(1-3), pp. 619-629 1996.

Lakshman, Mahesh K. Synthesis of Biologically Important Nucleoside Analogs by Palladium-Catalyzed C-N Bond-Formation. Current Organic Synthesis, 2005, 2, pp. 83-112.

* cited by examiner

CONVERTIBLE NUCLEOSIDE DERIVATIVES

CROSS-REFERENCE TO RELATED APPLICATIONS

This application is the U.S. National Phase of, and Applicants claim priority from, International Application Number PCT/US07/21808 filed Oct. 12, 2007, which claims priority from U.S. Provisional Application No. 60/829,168, filed Oct. 12, 2006 and U.S. Provisional Application No. 60/895,761, filed Mar. 20, 2007, all of which are incorporated herein by reference.

This invention was supported by the National Science Foundation, grant number CHE-0314326. The United States government has rights in the invention.

BACKGROUND OF THE INVENTION

Due to the high pharmacological, biological, biochemical, and diagnostic importance of nucleosides, facile methods for their modification is critical. $S_NAr$ displacement chemistry is a means of modifying nucleosides wherein a leaving group from the purine base is displaced by a suitable nucleophile.

Many compounds have resulted from $S_NAr$ displacement chemistry of nucleosides, ranging from adenosine receptor modifiers, anti-viral and anti-cancer agents, to carcinogen-nucleoside conjugates. These compounds have utilities ranging from potential pharmaceutical agents to probes of cellular response such as cancer causation. FIG. 1 shows some examples of modified nucleosides that have been synthesized using $S_NAr$ displacement chemistry.

Figure 1.
Compounds that have been synthesized by $S_NAr$ displacement reactions.

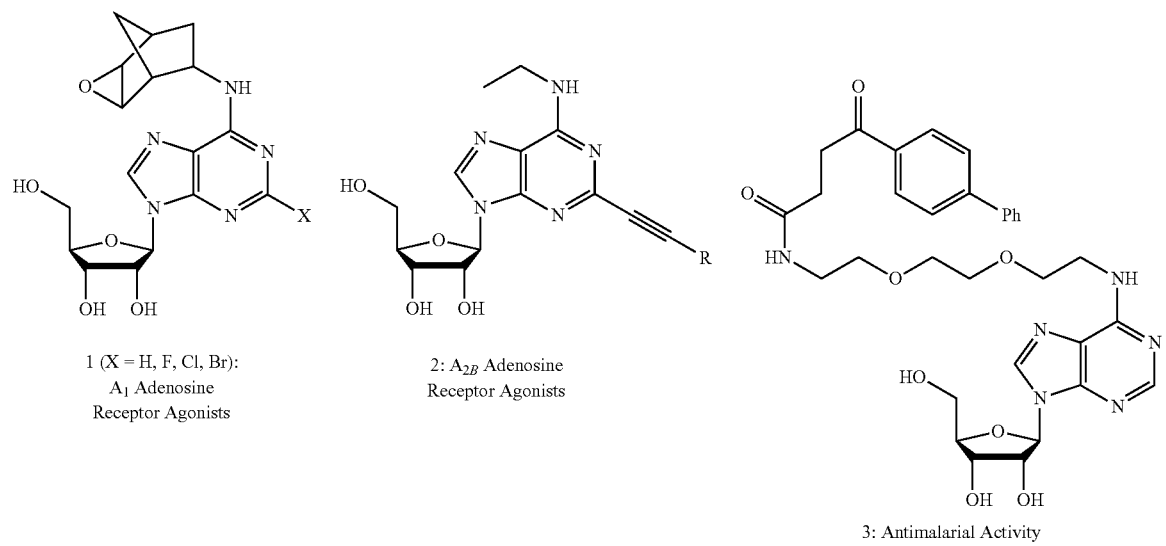

1 (X = H, F, Cl, Br):
$A_1$ Adenosine
Receptor Agonists

2: $A_{2B}$ Adenosine
Receptor Agonists

3: Antimalarial Activity

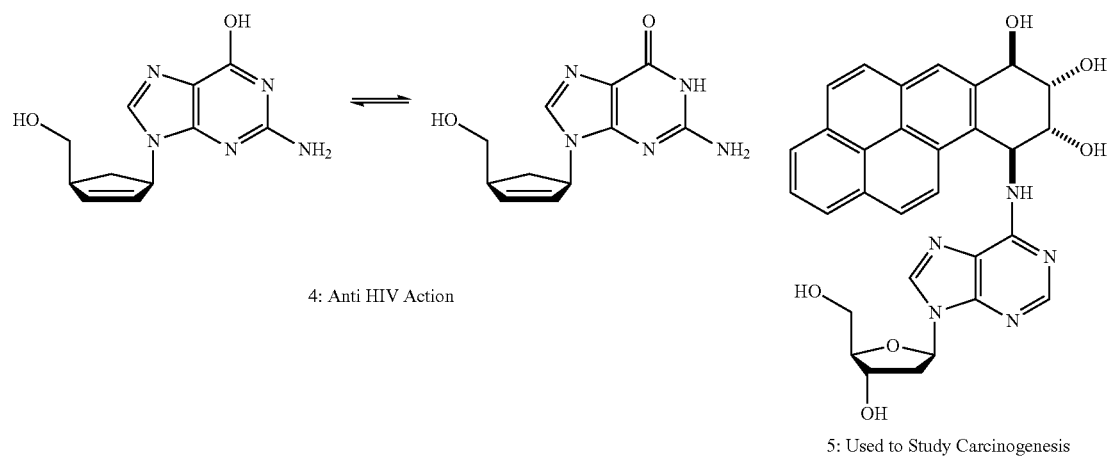

4: Anti HIV Action

5: Used to Study Carcinogenesis

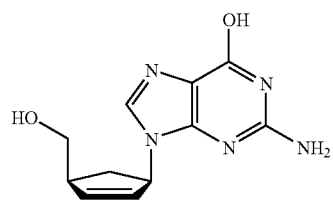 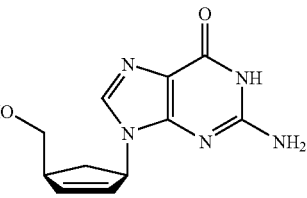 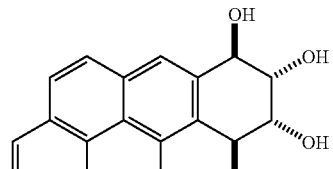

4: Anti HIV Action

5: Used to Study Carcinogenesis

Among the compounds in FIG. 1, compounds 1 and 2 were shown to be potent and selective adenosine $A_1$ and $A_{2B}$ receptor agonists. Adenosine receptors are of high importance in cardiac, nervous system functions as well as immune systems. Compound 3 was shown to be active against the malarial parasite Plasmodium falciparum. Carbovir, compound 4, showed promising activity as an anti HIV drug and the carcinogen-nucleoside conjugate has been used to probe DNA damage structure in the search for the underlying cause of carcinogenesis.

$S_NAr$ displacement reactions on nucleosides are an important transformation for the synthesis of new nucleosides with a significant variety of applications. Convertible nucleosides that can be used for such chemistry include 6-halo nucleosides and in some cases arylsulfonyl derivatives of nucleosides.

Structures of typical convertible purine nucleosides are shown in FIG. 2. These compounds could be either in the ribo nucleoside or the deoxyribonucleoside series (leading to new ribo or deoxyribonucleosides). Alternatively, any other entity can be attached to the 9-position of a purine that contains a leaving group at position 6 (leading to substituted purine derivatives).

Figure 2.
Structures of typical electrophilic convertible nucleosides.

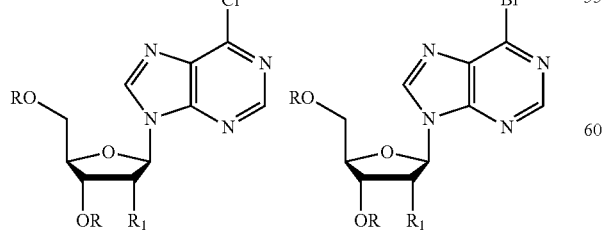

6: $R_1$ = OR
7: $R_1$ = H

8: $R_1$ = OR
9: $R_1$ = H

-continued

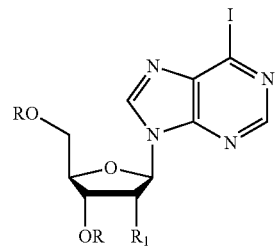

10: $R_1$ = OR
11: $R_1$ = H

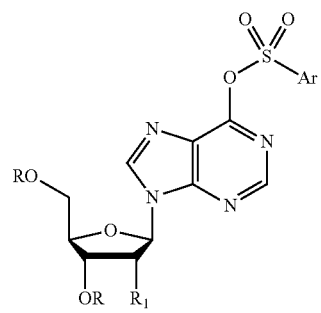

12: $R_1$ = OR
13: $R_1$ = H

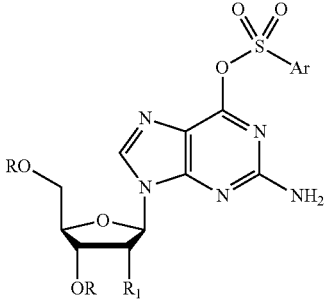

14: $R_1$ = OR
15: $R_1$ = H

R = Any protecting group or H
Ar = Any substituted aryl ring

Among the halo nucleosides shown in FIG. 2, compounds 6 and 7 (R═H) are commercially available. Compound 7 is relatively expensive. Compounds 6 and 7 can be synthesized via known procedures, but the methodology involved is quite difficult. The bromo and iodo nucleosides, which are not commercially available, are easier to prepare than the chloro analogs, however, the syntheses are not simple.

The aryl sulfonate derivatives (compounds 12-15), which are not commercially available, also require relatively non-trivial syntheses. In particular, the aryl sulfonylation reactions of hypoxanthine nucleosides that lead to compounds 12 and 13 are quite complex. For example, in the absence of an amino group at the C-2 position, sulfonylation of the hypoxanthine core produces a significant amount of the N-1 sulfonyl derivative which results in a substantial loss of a costly precursor.

Some other nucleoside derivatives shown in FIG. 3 have been developed as convertible nucleosides. For examples of the syntheses, see Fathi et al., Tetrahedron Lett., 31, 319-322 (1990); Ferentz et al., Nucleosides & Nucleotides, 11, 1749-1763 (1992); Gao et al., J. Org. Chem., 57, 6954-6959 (1992); Zemlicka et al., Nucleosides & Nucleotides, 15, 619-629 (1996); Mechtild et al., J. Chem. Soc., Perkin Trans. 1: Org. Bio-Org. Chem., 1825-1828 (1997); Maruenda et al., J. Org. Chem., 63, 4385-4389 (1998). These compounds are either derived from the types of compounds shown in FIG. 2 or require independent syntheses, none of which are simple and/or readily scalable.

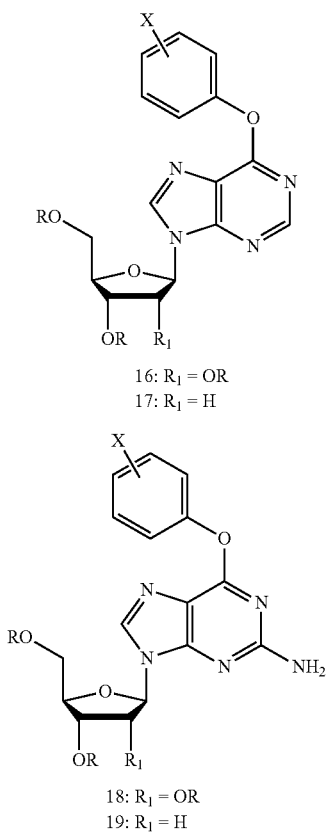

Figure 3. Structures of other convertible nucleosides.

16: $R_1$ = OR
17: $R_1$ = H

18: $R_1$ = OR
19: $R_1$ = H

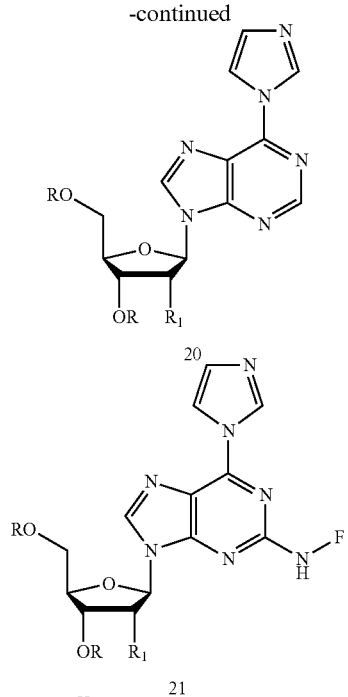

R = Any protecting group or H
X = Any substituent on the aryl ring
P = Trityl, MMT or DMT Recently it was shown that triphenylphosphine ($PPh_3$) in combination with iodine ($I_2$), N,N-diisopropylethyl amine (DIPEA) and either morpholine, piperidine or imidazole resulted in the conversion of hypoxanthine nucleosides to substituted adenine derivatives. See Lin et al., Org. Lett., 2, 3497-3499 (2000). Among these the imidazobil derivative 20 was found to be a useful convertible nucleoside. Subsequently, compound 21 was synthesized through a procedure similar to that leading to compound 20. The mechanism of this transformation is shown in Reaction Scheme 1. See Janeba et al., Nucleosides Nucleotides & Nucleic Acids, 7, 5877-5880 (2005).

Reaction Scheme 1
Synthesis of N,N-disubstituted adenine nucleosides.

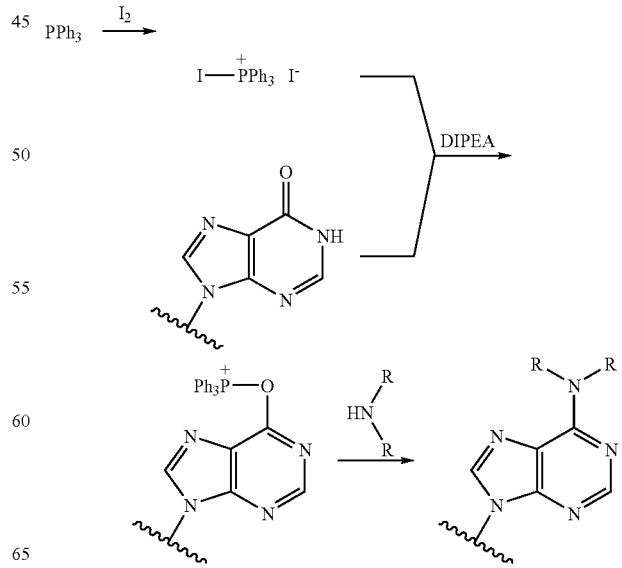

Of key importance in Reaction Scheme 1 was the formation of the phosphonium salt which functioned as a convertible nucleoside, and which was formed in situ. Subsequently, the use of 1H-benzotriazol-1-yloxy-tris(dimethylamino)phosphonium hexafluorophosphate (BOP), a peptide coupling agent, was reported for the activation of hypoxanthine nucleosides (Reaction Scheme 2). See Wan et al., Org. Lett., 7, 5877-5880 (2005).

Reaction Scheme 2
Use of BOP to activate hypoxanthine nucleosides.

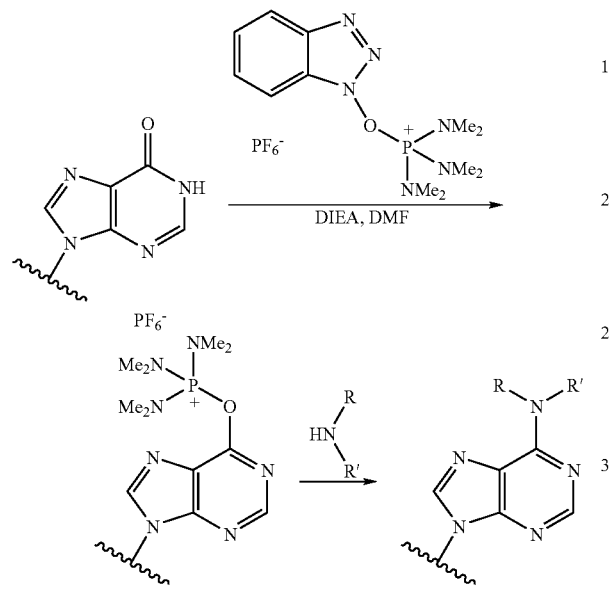

Convertible nucleosides are typically difficult to synthesize, and their prices are high as a result. Consequently, there is a need for convertible nucleosides that can be synthesized through the use of commercially available materials in an operationally simple and efficient protocol.

Embodiments of the Invention

In one embodiment, the invention related to a molecule having the formula ZOR, wherein:
Z represents:

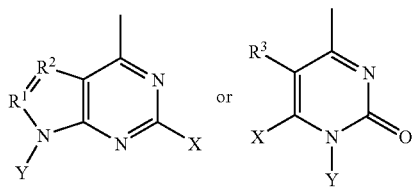

R represents:

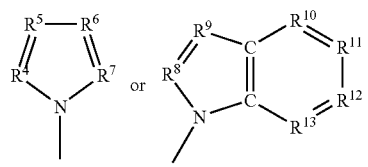

$R^1$ and $R^2$ independently represent $CR^3$ or N;
$R^4$, $R^5$, $R^6$, $R^7$, $R^8$, $R^9$, $R^{10}$, $R^{11}$, $R^{12}$, and $R^{13}$ represent, independently, N or CQ, with the proviso that no more than three of $R^4$, $R^5$, $R^6$, $R^7$ represents N;

X represents $R^{14}$, —$OR^{15}$, $SR^{15}$, —$N(R^{14})_2$, $R^{14}C(O)$—, nitro, or halo;
Q and $R^3$, independently of each other, and independently at each position, represent $R^{14}$, —$OR^{15}$, —$SR^{15}$, —$N(R^{14})_2$, $R^{14}C(O)$—, nitro, or halo;
Y represents $R^{14}$ or a saccharide moiety;
$R^{14}$ independently represents H, an alkyl group, a carbocyclic aryl group, or a heterocyclic aryl group;
$R^{15}$ independently represents $R^{14}$ or a protecting group;
wherein:
  alkyl groups are branched or unbranched and have 1-18 carbon atoms;
  alkyl groups are optionally substituted with halo groups;
  carbocyclic aryl groups have a total of 6-20 carbon atoms, including carbon atoms of substituents;
  heterocyclic aryl groups have a total of 5-20 carbon atoms, including carbon atoms of substituents;
  carbocyclic aryl groups and heterocyclic aryl groups are unsubstituted, or optionally substituted at any position with one or more of $R^{14}$, —$OR^{15}$, —$SR^{15}$, —$N(R^{14})_2$, $R^{14}C(O)$—, nitro, or halo.

In another embodiment, the invention related to a molecule having the formula Z—O—R-(L)$_n$-Po, wherein:
Z represents:

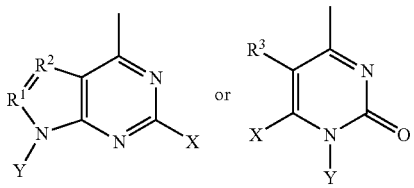

R represents:

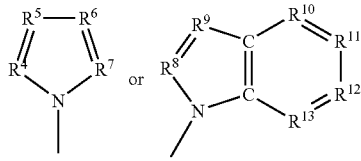

$R^1$ and $R^2$ independently represent $CR^3$ or N;
$R^4$, $R^5$, $R^6$, $R^7$, $R^8$, $R^9$, $R^{10}$, $R^{11}$, $R^{12}$, and $R^{13}$ represent, independently, N or CQ, with the proviso that no more than three of $R^4$, $R^5$, $R^6$, $R^7$ represents N;
X represents $R^{14}$, —$OR^{15}$, —$SR^{15}$, —$N(R^{14})_2$, $R^{14}C(O)$—, nitro, or halo;
Q and $R^3$, independently of each other, and independently at each position, represent $R^{14}$, —$OR^{15}$, —$SR^{15}$, —$N(R^{14})_2$, $R^{14}C(O)$—, nitro, or halo;
Y represents $R^{14}$ or a saccharide moiety;
$R^{14}$ independently represents H, an alkyl group, a carbocyclic aryl group, or a heterocyclic aryl group;
$R^{15}$ independently represents $R^{14}$ or a protecting group
wherein:
  alkyl groups are branched or unbranched and have 1-18 carbon atoms;
  alkyl groups are optionally substituted with halo groups;
  carbocyclic aryl groups have a total of 6-20 carbon atoms, including carbon atoms of substituents;
  heterocyclic aryl groups have a total of 5-20 carbon atoms, including carbon atoms of substituents;
  carbocyclic aryl groups and heterocyclic aryl groups are unsubstituted, or optionally substituted at any position with one or more of $R^{14}$, —$OR^{15}$, —$SR^{15}$, —$N(R^{14})_2$, $R^{14}C(O)$—, nitro, or halo;

L represents any chain of up to 20 atoms selected from carbon, nitrogen, oxygen, or sulfur
wherein:
the carbon atom is —$CH_2$—, —C(O)—, or phenyl;
the nitrogen atom is —N($R^{14}$)—,
the oxygen atom is —O—,
the sulfur atom is —S($O_2$)—;
n is 0 or 1; and
Po represents an organic polymer, an inorganic polymer, or combinations thereof.

In yet another embodiment, the invention related to a molecule having the formula ZOR, wherein:
Z represents:

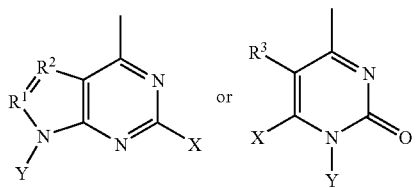

R represents:

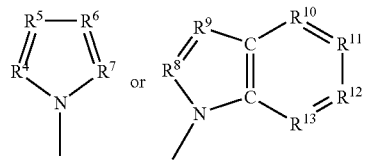

$R^1$ and $R^2$ independently represent $CR^3$ or N;
$R^4$, $R^5$, $R^6$, $R^7$, $R^8$, $R^9$, $R^{10}$, $R^{11}$, $R^{12}$, and $R^{13}$ represent, independently, N or CQ, with the proviso that no more than three of $R^4$, $R^5$, $R^6$, $R^7$ represents N;
X represents $R^{14}$, —$OR^{15}$, $SR^{15}$, —N($R^{14}$)$_2$, $R^{14}$C(O)—, nitro, or halo;
Q and $R^3$, independently of each other, and independently at each position, represent $R^{14}$, —$OR^{15}$, —$SR^{15}$, —N($R^{14}$)$_2$, $R^{14}$C(O)—, nitro, or halo;
Y represents a saccharide moiety having the following structure:

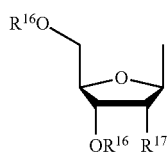

$R^{14}$ independently represents H, an alkyl group, a carbocyclic aryl group, or a heterocyclic aryl group;
$R^{15}$ independently represents $R^{14}$ or a protecting group;

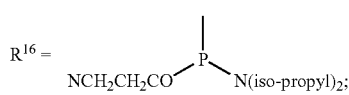

$R^{17}$ is hydrogen; and
$R^{18}$ is hydrogen or a protecting group;

wherein:
alkyl groups are branched or unbranched and have 1-18 carbon atoms;
alkyl groups are optionally substituted with halo groups;
carbocyclic aryl groups have a total of 6-20 carbon atoms, including carbon atoms of substituents;
heterocyclic aryl groups have a total of 5-20 carbon atoms, including carbon atoms of substituents;
carbocyclic aryl groups and heterocyclic aryl groups are unsubstituted, or optionally substituted at any position with one or more of $R^{14}$, —$OR^{15}$, —$SR^{15}$, —N($R^{14}$)$_2$, $R^{14}$C(O)—, nitro, or halo.

ABBREVIATIONS

Abbreviations used throughout the specification are defined as follows:
BOP, 1H-benzotriazol-1-yloxy-tris(dimethylamino)phosphonium hexafluorophosphate
BOPNuc, BOP nucleoside derivatives
BroP, Bromo-tris-(dimethylamino)phosphonium hexafluorophosphate
DIPEA, N,N-diisopropylethylamine
DME, 1,2-dimethoxyethane
DMF, N,N-dimethylformamide
DMT, 4,4'-dimethoxytrityl
HMPT, hexamethylphosphorus triamide
HOBT, anhydrous 1-hydroxybenzotriazole
MMT, monomethoxytrityl
PS-HOBT, 1-hydroxybenzotriazole-6-sulfonamidomethyl polystyrene
PyBroP, bromo-tris-pyrrolidinophosphonium hexafluorophosphate
TBDMS, tert-butyldimethylsilyl
THF, tetrahydrofuran

DETAILED DESCRIPTION OF THE INVENTION

The invention relates to convertible nucleosides for use in $S_NAr$ displacement reactions. The nucleosides can be used to synthesize numerous substituted purine and pyrimidine derivatives.

The molecules have the formula ZOR. In this formula, Z represents:

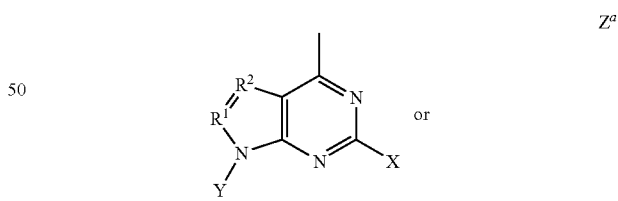

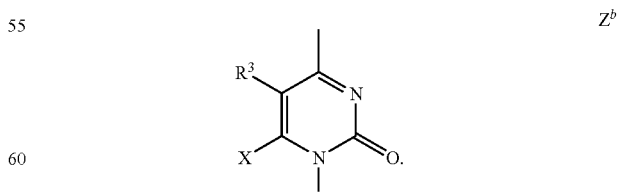

When Z is $Z^a$, $R^1$ and $R^2$ independently represent $CR^3$ or N. For example, $R^1$ represents $CR^3$ and $R^2$ represents N; $R^1$ represents N and $R^2$ represents $CR^3$; $R^1$ represents N and $R^2$ represents N; and $R^1$ represents $CR^3$ and $R^2$ represents $CR^3$.

In a preferred embodiment, $R^1$ represents $CR^3$ and $R^2$ represents N. $R^3$ is as described below.

In the above formulas, X represents $R^{14}$, —$OR^{15}$, $SR^{15}$, —$N(R^{14})_2$, $R^{14}C(O)$—, nitro, or halo. Y represents $R^{14}$ or a saccharide moiety. $R^{14}$, $R^{15}$, and a saccharide moiety are as described below.

In the formula ZOR, R represents:

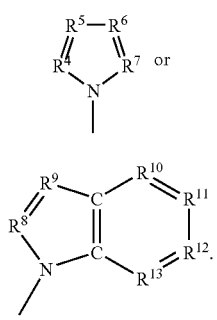

In this specification, unless otherwise defined, the following definitions apply. $R^4$, $R^5$, $R^6$, $R^7$, $R^8$, $R^9$, $R^{10}$, $R^{11}$, $R^{12}$, and $R^{13}$ represent, independently, N or CQ.

When R is $R^a$, no more than three of $R^4$, $R^5$, $R^6$, and $R^7$ represent N. For example, $R^4$, $R^5$, $R^6$, and $R^7$ may represent CQ. In a preferred embodiment, $R^5$ represents N and $R^4$, $R^6$, and $R^7$ represent CQ.

R preferably represents $R^b$. In one embodiment, $R^8$ and $R^9$ represent N. In another embodiment, $R^8$, $R^9$, and $R^{13}$ represent N.

Preferably, when R represents $R^b$, no more than one of $R^{10}$, $R^{11}$, $R^{12}$, and $R^{13}$ represent N. For example, $R^{10}$, $R^{11}$ and $R^{12}$ may represent CQ and $R^{13}$ may represent N; or $R^{10}$, $R^{11}$, $R^{12}$, and $R^{13}$ may represent CQ. In a particularly preferred embodiment, R represents $R^b$, $R^8$ and $R^9$ represent N, and $R^{10}$, $R^{11}$, $R^{12}$, and $R^{13}$ represent CQ.

Q and $R^3$, independently of each other, and independently at each position, represent $R^{14}$, —$OR^{15}$, —$SR^{15}$, —$N(R^{14})_2$, $R^{14}C(O)$—, nitro, or halo. In this specification, halo includes, fluoro, chloro, bromo, or iodo.

$R^{14}$ independently represents H, alkyl groups, carbocyclic aryl groups, or heterocyclic aryl groups. In a preferred embodiment, $R^{14}$ represents H.

$R^{15}$ independently represents $R^{14}$ or a protecting group. Protecting groups are as described below. In a preferred embodiment, $R^{15}$ represents an alkyl group.

In this specification, alkyl groups are branched or unbranched, and have a minimum of one, two, or three carbon atoms. The maximum number of carbon atoms is eighteen, sixteen, or twelve.

Some examples of suitable straight-chained alkyl groups include methyl, ethyl, n-propyl, n-butyl, n-pentyl, n-hexyl groups and dodecyl and hexadecyl. Preferred straight chain alkyl groups include methyl and ethyl.

Some examples of suitable branched alkyl groups include iso-propyl, iso-butyl, sec-butyl, t-butyl, 1-methylbutyl, 2-methylbutyl, 3-methylbutyl (isopentyl), 1,1-dimethylpropyl, 1,2-dimethylpropyl, 2,2-dimethylpropyl(neopentyl), 1-methylpentyl, 2-methylpentyl, 3-methylpentyl, 4-methylpentyl groups, and 2-methyl, 5-ethyldecyl. Preferred branched alkyl groups include isopropyl and t-butyl.

The alkyl groups are optionally substituted with halo groups. Some examples of suitable haloalkyl groups include trifluoromethyl, 2,2,2-trichloroethyl, 2-bromoethyl, 2-chloropropyl, and 3-bromopropyl.

Carbocyclic aryl groups can be unfused or fused. A preferred unfused carbocyclic aryl group is phenyl. Some examples of other fused carbocyclic aryl groups include naphthyl, phenanthryl, anthracenyl, triphenylenyl, chrysenyl, and pyrenyl.

Heterocyclic aryl groups contain one or more ring heteroatoms, e.g., nitrogen, oxygen, or sulfur atoms, and may be unfused or fused. Some examples of unfused heterocyclic aryl groups include thiophenyl, furyl, pyrrolyl, pyrazolyl, imidazolyl, oxazolyl, thiazolyl, pyridinyl, pyridazinyl, pyrimidinyl, and pyrazinyl. Some examples of fused heterocyclic aryl groups include purinyl, 1,4-diazanaphthalenyl, indolyl, benzimidazolyl, 4,5-diazaphenanthrenyl, and benzoxazolyl.

Carbocyclic and heterocyclic aryl groups may be, unsubstituted, or are optionally substituted at any position with one or more substituents. Some examples of aryl substituents include $R^{14}$, —$OR^{15}$, —$SR^{15}$, —$N(R^{14})_2$, $R^{14}C(O)$—, nitro, or halo.

Carbocyclic aryl groups contain a minimum of six carbon atoms. The maximum number of carbon atoms is twenty, including carbon atoms, if any, of optional substituents and/or fused rings.

Heterocyclic aryl groups contain a minimum of five carbons. The maximum number of carbon atoms is twenty carbon atoms, including carbon atoms, if any, of optional substituents and/or fused rings.

Saccharides which can be used in this invention can be any monosaccharide or polysaccharide. Preferred polysaccharides include disaccharides and trisaccharides. The maximum number of saccharides in a polysaccharide is typically ten, preferably five. The saccharides can be in either the D or L configuration. Monosaccharides can be either aldoses or ketoses. The number of carbons of the saccharide can be from three carbons to about six carbons. An example of a three carbon sugar is glyceraldehyde. Examples of four carbon sugars include erythrose and threose. Examples of five carbon sugars include ribose, arabinose, xylose and lyxose. Examples of six carbon sugars include allose, altrose, glucose, mannose, gulose, idose, galactose and talose. Saccharides further include the corresponding 2'-deoxy derivatives.

In a particular embodiment of the invention, Y is a ribose or 2'-deoxyribose moiety, preferably having the following structure:

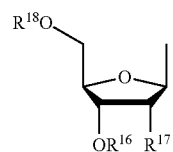

wherein $R^{16}$ represents H or a protecting group; $R^{17}$ represents H or $OR^{16}$; and $R^{18}$ represents $R^{15}$. Preferably, $R^{18}$ represents $R^{16}$ or an alkyl group. The alkyl group is preferably methyl or ethyl.

In this specification, protecting groups can be essentially any group suitable for the protection of a hydroxyl group, as known in the art. The phrase "protecting group" indicates any functionality that is used to replace a hydrogen atom on an alcohol, and which can easily be removed with restoration of the hydrogen without altering the structure of the remainder of the molecule.

Protecting groups are reviewed in *Protecting groups* by Kocienski, Philip J. Stuttgart, New York, Georg Thieme, 2005; and in *Protective groups in organic synthesis* by Greene, Theodora W. and Wuts, Peter G. M. New York, Wiley, 1999. Some examples are given below, but are not meant to be inclusive.

A class of useful protecting groups for compounds of the invention is the acetal/ketal class. This class of protecting groups can be represented according to the formula: —C(OR$^{19}$)(R$^{20}$)(R$^{21}$).

R$^{19}$ is preferably an alkyl group, R$^{20}$ is preferably an alkyl group, an aryl group, or a hydrogen atom, and R$^{21}$ is preferably an alkyl group or a hydrogen atom. The alkyl groups of R$^{19}$, R$^{20}$, and R$^{21}$ may be any of those described above, and preferably have one to four carbon atoms, typically methyl or ethyl. The alkyl groups of R$^{19}$ and R$^{20}$ may also be joined to form a five or six member saturated ring. The aryl group of R$^{20}$ may be any carbocyclic or heterocyclic aryl group described above, and is preferably phenyl, pyridinyl, pyrrolyl, or furanyl. Some preferred acetal/ketal protecting groups include methoxymethyl, ethoxymethyl, tetrahydropyranyl, and benzyloxymethyl.

Another example of a class of suitable protecting groups for R$^{15}$ includes the class of silyl protecting groups. The class of silyl protecting groups can be represented according to the formula: —Si(O$_x$R$^{22}$)(O$_y$R$^{23}$)(O$_z$R$^{24}$).

In the formula above for silyl protecting groups, R$^{22}$, R$^{23}$, and R$^{24}$ each independently represents any of the alkyl groups or carbocyclic or heterocyclic aryl groups described above. The subscripts x, y, and z independently represent 0 or 1. When x, y, or z is 0, then the oxygen atom to which the subscript is associated is absent. When x, y, or z is 1, then the oxygen atom to which the subscript is associated, is present.

Some examples of silyl protecting groups wherein x, y, and z are all 0, include triethylsilyl, tri-(n-propyl)silyl, triisopropylsilyl, tri-(n-butyl)silyl, triisobutylsilyl, t-butyldimethylsilyl, t-butyldiphenylsilyl, phenyldimethylsilyl, methyldiphenylsilyl, and triphenylsilyl. Some examples of silyl protecting groups wherein at least one of x, y, and z is 1, include trimethoxysilyl, dimethoxymethylsilyl, methoxydimethylsilyl, trifluoromethoxymethylsilyl, ethoxydimethylsilyl, methoxydiethylsilyl, isopropoxydimethylsilyl, phenoxydimethylsilyl, phenoxydiethylsilyl, methyldiphenoxysilyl, [2,4,6-tri-(t-butyl)phenoxy]dimethylsilyl, t-butoxydimethylsilyl, t-butoxydiphenylsilyl, t-butylmethoxyphenylsilyl, and methoxydiphenylsilyl.

Another example of a class of suitable protecting groups includes arylmethyl protecting groups, which protect a hydroxyl group by converting it to an arylmethyl ether. The aryl group may be any of the carbocyclic or heterocyclic aryl groups described above. Some examples of preferred aryl groups include phenyl, pyridinyl, pyrrolyl, or furanyl, optionally substituted with methoxy, ethoxy, nitro, or halo (F, Cl, Br, or I). Some preferred members of this class of protecting groups include benzyl, p-methoxybenzyl, and p-ethoxybenzyl.

Trityl ethers are another class of suitable protecting group. Some examples of trityl ethers include monomethoxy trityl ether, dimethoxytrityl ether, and trimethoxy trityl ether.

In a preferred embodiment of the invention, Z represents:

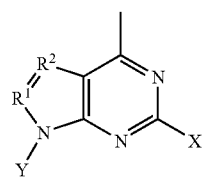

R represents:

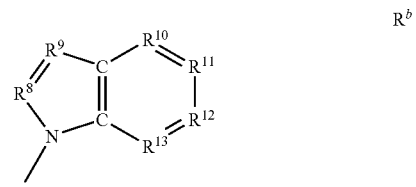

R$^1$ represents CR$^3$ and R$^3$ represents H; R$^2$, R$^8$, and R$^9$ represent N; R$^{10}$, R$^{11}$, R$^{12}$, and R$^{13}$ represent CQ; Q and X represent R$^{14}$ and R$^{14}$ represents H;

Y represents a saccharide moiety, with the following structure:

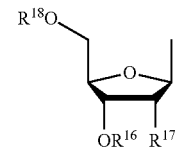

wherein R$^{16}$ represents H or a protecting group; R$^{17}$ represents H or OR$^{16}$; and R$^{18}$ represents R$^{16}$ or an alkyl group. The alkyl group is preferably methyl or ethyl.

In another embodiment, the chemistry described herein can be adapted wherein convertible nucleoside derivatives are assembled onto a polymer support. These polymer supported derivatives can be used in diversity-oriented and high-throughput syntheses such as combinatorial libraries and for parallel array reactions. Both methods are aimed at the rapid production of large numbers of small molecules predominantly for pharmacological screening. Polymer supported derivatives have found significant use in multi-step organic synthesis as well.

Accordingly, in an additional embodiment, the invention relates to polymer-supported convertible nucleoside derivatives of the formula Z—O—R-(L)$_n$-Po. Z and R are as described above.

Po represents an organic polymer, an inorganic polymer, or a combination thereof. Examples of organic polymers include polyethylene glycol, polystyrene, and amino resins. In a preferred embodiment, the organic polymer is a polystyrene such as 1% cross-linked polystyrene-co-divinylbenzene. Inorganic polymers include glass beads, silica gel, alumina, controlled pore glass, and amino-modified controlled pore glass.

Organic polymers and inorganic polymers may be combined to form a composite where an inorganic support is linked to an organic polymer. For example, polyethylene glycol may be linked to glass beads.

Po can be attached to R at either R$^4$, R$^5$, R$^6$, R$^7$, R$^8$, R$^9$, R$^{10}$, R$^{11}$, R$^{12}$, R$^{13}$. The polymer can be attached directly to R or to R through a linker, L.

The letter n represents 0 or 1.

Linker, L, is any chain of up to twenty atoms selected from carbon, nitrogen, oxygen, or sulfur. The carbon atom is in the form of —CH$_2$—, —C(O)—, or positions 1-4 of a phenyl group. The nitrogen atom is in the form of —N(R$^{14}$)—. The oxygen atom is in the form of —O—. The sulfur atom is in the form of —S(O$_2$)—.

For example, the linker, L, may be represented by -(A$^1$)$_a$-(A$^2$)$_b$-(A$^3$)$_c$-(Ph)$_k$. Each of A$^1$, A$^2$, and A$^3$ is different from the others, and independently represents —CH$_2$—, —C(O)—, —O—, —N(R$^{14}$)—, or —S(O$_2$)—. Ph represents phenyl. The letters a, b, and c are independently 0, 1, or 2. The letter k represents 0 or 1. R$^{14}$ is as described above.

Preferably, at least one of a, b, and c is not 0. For example, if a and b are 0, then c is not 0.

For example:
when A$^1$ represents —S(O$_2$)—; A$^2$ represents —N(R$^{14}$)—; A$^3$ represents —CH$_2$—; a, b, c, k, and n are 1; and R$^{14}$ is H, the resulting structure for -(L)$_n$-Po is

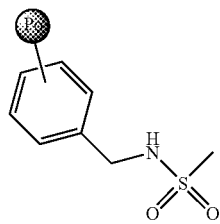

when A$^1$ represents —C(O)—; A$^2$ represents —N(R$^{14}$)—; A$^3$ represents —CH$_2$—; a, b, c, k, and n are 1; and R$^{14}$ is H, the resulting structure for -(L)$_n$-Po is

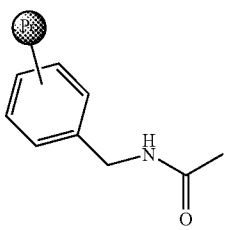

In another embodiment, L is represented by -(A$^1$-A$^2$)$_{m1}$-(CH$_2$)$_{m2}$-(Ph)$_k$-. Each A$^1$ and A$^2$ is different from the other, and independently represents —C(O)—, —O—, —N(R$^{14}$)—, or —S(O$_2$)—. Ph represents phenyl. The letters m1 and k are independently 0 or 1 and m2 is 0, 1, or 2. R$^{14}$ is as described above.

Preferably, at least one of m1 and m2 is not 0. For example, if m1 is 0 then m2 is not 0.

Synthesis of Convertible Nucleoside Derivatives

Nucleosides may be converted to the convertible derivatives of the invention by treatment with a suitable phosphonium ion and a sterically hindered amine. Suitable phosphonium ions include R$^b$—O—P$^+$T$_3$.A$^-$, where T is N(lower alkyl)$_2$, phenyl, substituted phenyl, or the alkyl groups join to form a heterocyclic ring. Examples of such heterocyclic rings include pyrrolidine, piperidine, and morpholine. Lower alkyl groups are C$_1$-C$_4$. A$^-$ is a counterion such as PF$_6$ or halide (F, Cl$^-$, Br$^-$, or I$^-$). R$^b$ is as described above. Sterically hindered amines include tertiary amines such as DIPEA, triethylamine, 1-methylmorpholine, and 1-methylpiperidine. These reactions may be carried out at room temperature for about 23 hours to about 68 hours. Some examples are illustrated in Reaction Scheme 3 and in the examples section.

For example, any hypoxanthine core can be converted to a BOPNuc analog so long as other functionalities that would react with BOP are absent. For example, the synthesis of BOPNuc derivatives is shown below in Reaction Scheme 3. The ribonucleoside precursor, BOP, DIPEA and THF were combined in a flask, then stirred at room temperature for 23 hours. The mixture was evaporated, washed with water, dried, concentrated, and purified via column chromatography to yield the corresponding ribonucleoside analog.

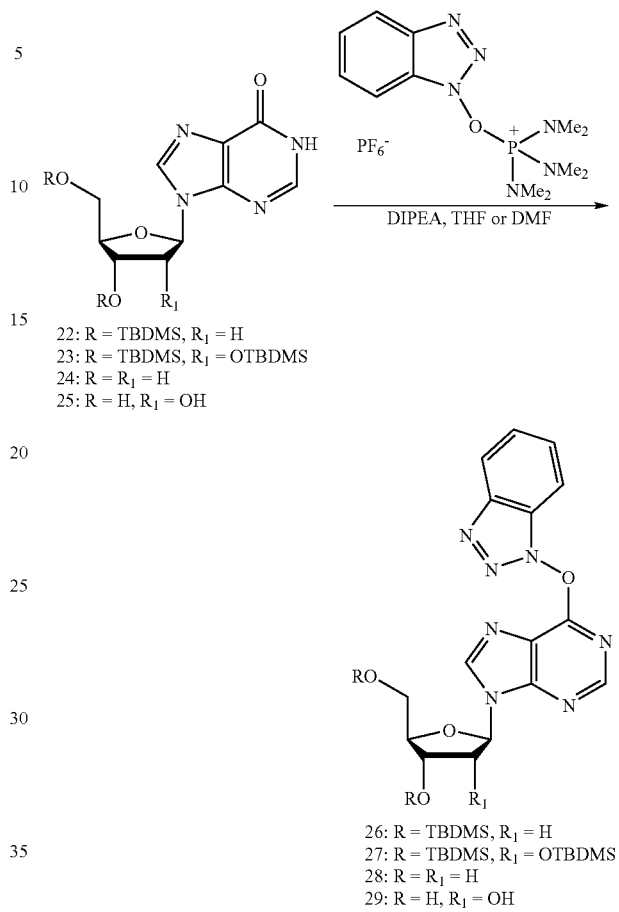

Reaction Scheme 3

22: R = TBDMS, R$_1$ = H
23: R = TBDMS, R$_1$ = OTBDMS
24: R = R$_1$ = H
25: R = H, R$_1$ = OH

26: R = TBDMS, R$_1$ = H
27: R = TBDMS, R$_1$ = OTBDMS
28: R = R$_1$ = H
29: R = H, R$_1$ = OH

For example, the ribonucleoside analog BOPNuc 27 was synthesized from the nucleoside precursor 23 (80% yield). Likewise, the hydroxyl unprotected deoxynucleoside 24 and the ribonucleoside 25 were readily converted to the BOPNuc 28 and 29 (in DMF as solvent), suggesting that no competing reaction occurs at the hydroxyl groups.

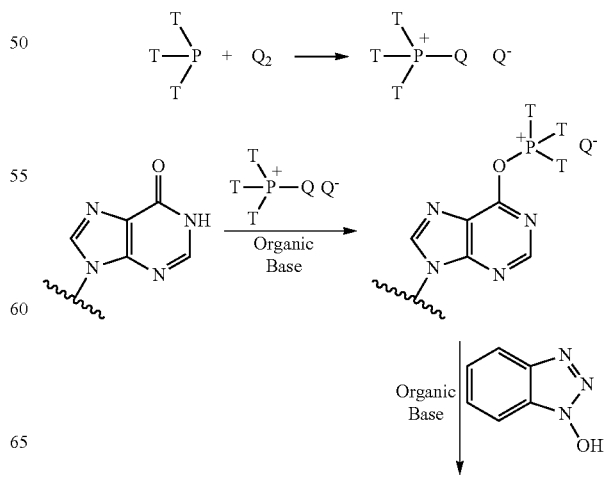

Reaction Scheme 4

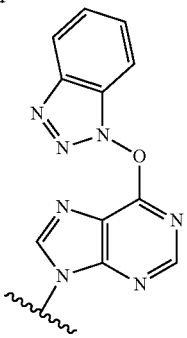

Alternatively, nucleosides may be converted to the convertible derivatives of the invention as seen in Reaction Scheme 4 above (or a related scheme with different, but analogous reactants.) First, a phosphine P-T$_3$, where T$_3$ is as described above, is reacted with a halogen. The halogen, Q$_2$, may be F$_2$, Cl$_2$, Br$_2$, or I$_2$. Preferably, Q$_2$ represents I$_2$. In a preferred embodiment, the phosphine is triphenylphospine.

The resulting phosphonium salt, Q-P$^+$T$_3$.Q$^-$ is reacted with a nucleoside precursor (Z$^a$O), e.g. compounds 22 or 23, in the presence of an organic base in an organic solvent. Suitable organic bases include DIPEA, triethylamine, and tributylamine. Examples of organic solvents include CH$_2$Cl$_2$, DMF, THF, and 1,2-dichloroethane. Displacement by R$^b$—OH (or R$^a$—OH), where R$^a$ and R$^b$ are as described above, in the presence of an organic base results in the desired convertible nucleoside derivatives. The synthesis is shown in Reaction Scheme 4 below.

Preferred conditions for conversion of compounds 22 and 23 to 26 and 27, respectively, involved a reaction between 1 molar equivalent of 22 or 23 with 3 molar equivalents of triphenylphosphine (PPh$_3$), 3 molar equivalents of I$_2$, 8 molar equivalents of diisopropylethyl amine (DIPEA) and 1.5 molar equivalents of HOBT in dichloromethane solvent. The products, compounds 26 and 27, were obtained in yields of 90-96% after purification.

Conversion of Nucleoside Derivatives

The convertible nucleoside derivatives of the invention can be converted to useful nucleoside derivatives by means of S$_N$Ar displacement reactions, as is known in the art. In order to demonstrate the versatility of BOPNuc compounds as convertible nucleosides, a series of solution-phase experiments were performed wherein BOPNuc derivatives 26 and 27 were subjected to a nucleophilic displacement with a variety of nitrogen (primary and secondary amines), oxygen (alcohol and phenol) and sulfur (thiol) nucleophiles. These are schematically represented in Reaction Scheme 5. The results are compiled in Table 1.

Reaction Scheme 5
Examples of the types of displacement reactions that can be conducted on convertible nucleoside derivatives 26 and 27

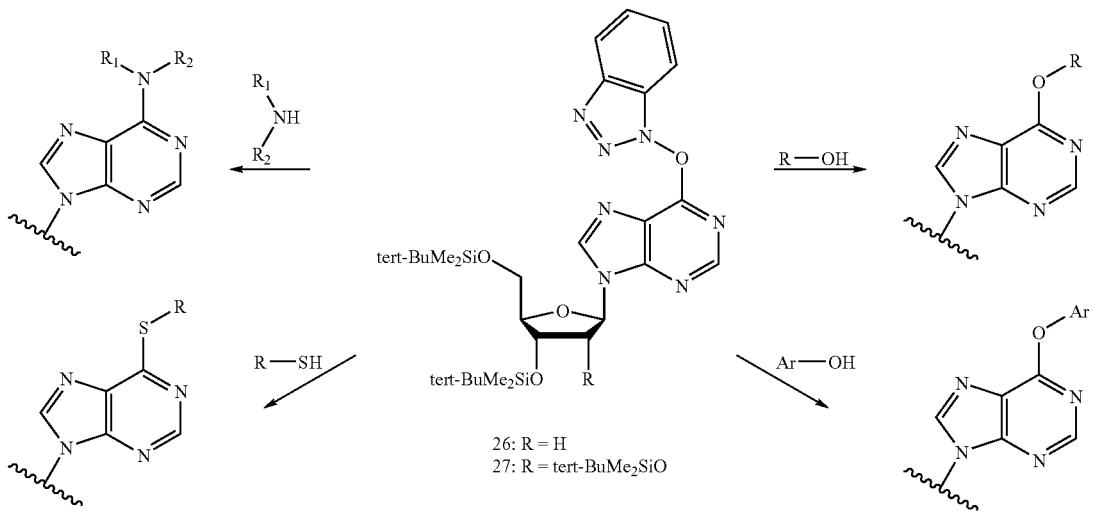

26: R = H
27: R = tert-BuMe$_2$SiO

TABLE 1

Results of displacement reactions with convertible nucleoside derivatives 26 and 27.

| Entry | BOPNuc | Nucleophile | Conditions | Product yield |
|---|---|---|---|---|
| 1 | 26 | CH$_3$OH | CH$_3$OH, Cs$_2$CO$_3$, rt, 1 h | 77% |
| 2 | 26 | CH$_3$CH$_2$OH | CH$_3$CH$_2$OH, Cs$_2$CO$_3$, rt, 1 h | 95% |
| 3 | 26 | (CH$_3$)$_2$CHOH | (CH$_3$)$_2$CHOH, Cs$_2$CO$_3$, rt, 10 h | 84% |
| 4 | 27 | (CH$_3$)$_2$CHOH | (CH$_3$)$_2$CHOH, Cs$_2$CO$_3$, rt, 24 h, then 82° C., 3 h | 70% |
| 5 | 26 | CH$_2$=CHCH$_2$OH | CH$_2$=CHCH$_2$OH, Cs$_2$CO$_3$, rt, 2 h | 89% |
| 6 | 26 | Ph—OH | PhMe, Cs$_2$CO$_3$, 105° C., 2 h | 86% |

TABLE 1-continued

Results of displacement reactions with convertible nucleoside derivatives 26 and 27.

| Entry | BOPNuc | Nucleophile | Conditions | Product yield |
|---|---|---|---|---|
| 7 | 26 | 4-nitrophenol (O$_2$N–C$_6$H$_4$–OH) | PhMe, Cs$_2$CO$_3$, 105° C., 20 h<br>DME, Cs$_2$CO$_3$, 85° C., 2 h | 75%<br>78% |
| 8 | 27 | 4-nitrophenol (O$_2$N–C$_6$H$_4$–OH) | DME, Cs$_2$CO$_3$, 85° C., 1 h | 81% |
| 9 | 26 | 3-cyanophenol | DME, Cs$_2$CO$_3$, 85° C., 2 h | 82% |
| 10 | 26 | 1-naphthol | DME, Cs$_2$CO$_3$, 85° C., 2 h | 81% |
| 11 | 26 | 2-hydroxyfluorene | DME, Cs$_2$CO$_3$, 85° C., 1 h | 87% |
| 12 | 26 | 8-hydroxyquinoline | DME, Cs$_2$CO$_3$, 85° C., 1 h | 79% |
| 13 | 27 | 8-hydroxyquinoline | DME, Cs$_2$CO$_3$, 85° C., 1 h | 72% |
| 14 | 26 | hydroquinone | DME, Cs$_2$CO$_3$, 85° C., 3 h | 68%[a] |
| 15 | 26 | Boc-Tyr-OMe | DME, Cs$_2$CO$_3$, 85° C., 1 h | 64%[b] |
| 16 | 26 | morpholine | DME, Cs$_2$CO$_3$, rt, 1 h<br>DME, rt, 1 h | 78%<br>52% |
| 17 | 27 | morpholine | DME, Cs$_2$CO$_3$, rt, 1 h<br>DME, rt, 1 h | 85%<br>90% |

TABLE 1-continued

Results of displacement reactions with convertible nucleoside derivatives 26 and 27.

| Entry | BOPNuc | Nucleophile | Conditions | Product yield |
|---|---|---|---|---|
| 18 | 28 | morpholine (NH) | DME, $Cs_2CO_3$, rt, 1 h | 52% |
| 19 | 29 | morpholine (NH) | DME, $Cs_2CO_3$, rt, 1 h | 58% |
| 20 | 26 | benzylamine ($PhCH_2NH_2$) | DME, $Cs_2CO_3$, rt, 6 h<br>DME, rt, 8 h | 84%<br>75% |
| 21 | 27 | benzylamine ($PhCH_2NH_2$) | DME, $Cs_2CO_3$, rt, 7 h<br>DME, rt, 9 h | 87%<br>83% |
| 22 | 26 | imidazole (NH) | DME, $Cs_2CO_3$, 85° C., 4 h | 60% |
| 23 | 26 | benzyl mercaptan ($PhCH_2SH$) | DME, $Cs_2CO_3$, rt, 1 h | 85% |
| 24 | 27 | benzyl mercaptan ($PhCH_2SH$) | DME, $Cs_2CO_3$, rt, 1 h | 93% |
| 25 | 26 | protected inosine derivative (tert-$BuMe_2SiO$ groups) | PhMe, $K_3PO_4$, 105° C., 3 h<br>DME, $Cs_2CO_3$, 85° C., 1 h | 92%[c]<br>60%[c] |

[a]Product is a dimer where both phenolic hydroxyls undergo etherification.
[b]It is plausible that some epimerization could have occurred at the chiral center since the starting amino acid does undergo partial racemization under the reaction conditions. However, the $^1$H NMR spectrum of the product does not show any resolved signals for the diastereomers.
[c]The N-1 of the nucleophile is attached to the C-6 of the substrate.

Other nucleophiles, such as azide, cyanide, selenides and carbanions ($sp^3$, $sp^2$, sp), etc., can also be effectively utilized as nucleophiles in $S_NAr$ reactions with convertible nucleoside derivatives. These nucleophiles result in intermediates that can be used for novel applications and for discovery of new compounds with biological, biochemical and pharmacological importance. Some examples are shown in Scheme 6.

Reaction Scheme 6
Other potential applications of convertible nucleoside analogs.

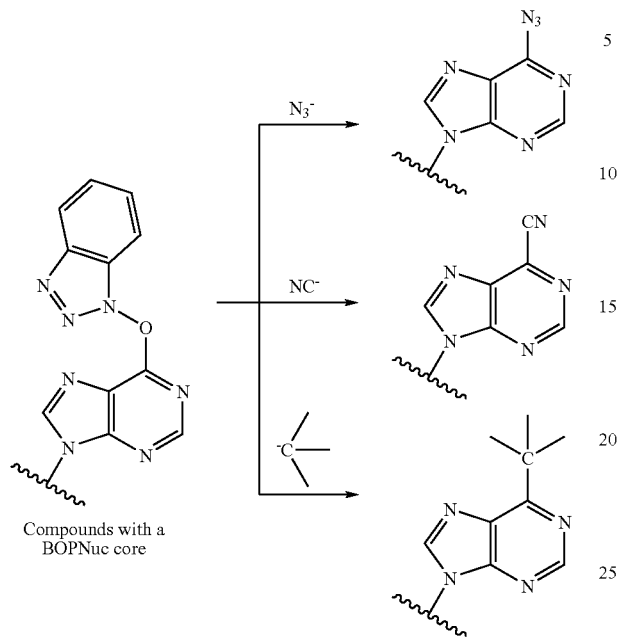

Compounds with a BOPNuc core

In addition to hypoxanthine cores, pyrimidine cores can also form convertible pyrimidine derivatives by, for example, reacting with BOP. In Reaction Scheme 7, the pyrimidine core, BOP, and NaH in dry THF are stirred at room temperature for 23 hours. The mixture is evaporated, washed with water, dried, concentrated, and purified via column chromatography to yield a convertible pyrimidine derivative.

Reaction Scheme 7
Application for the synthesis of pyrimidine based convertible
nucleoside derivatives and their applications for the synthesis of new pyrimidine derivatives.

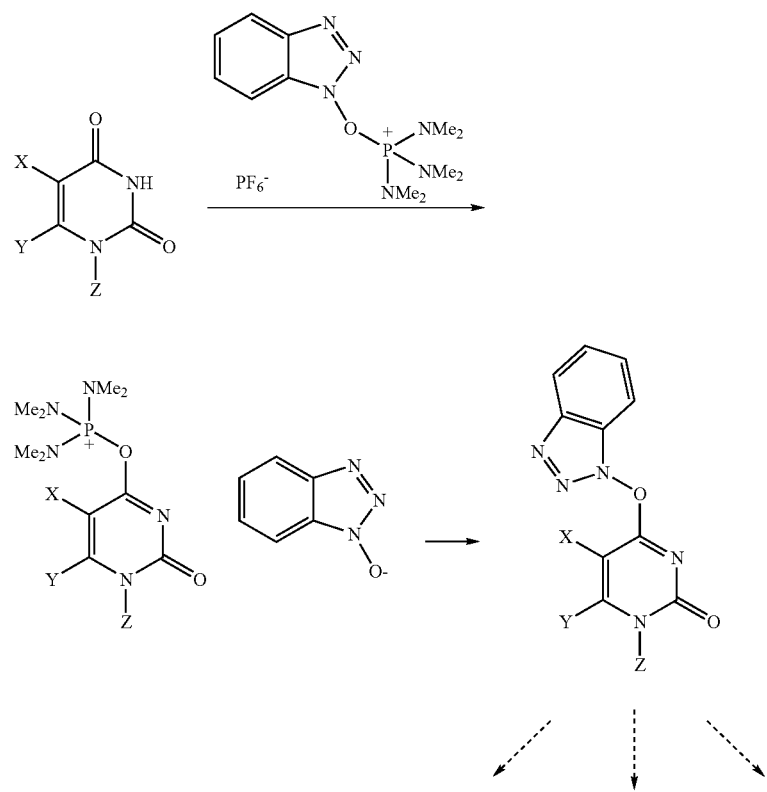

-continued

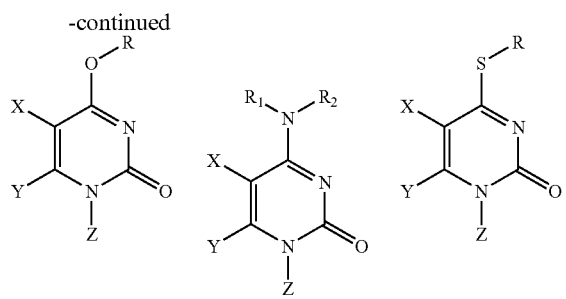

Synthesis of Polymer-Supported Convertible Nucleoside Derivatives

Any of the nucleoside precursors mentioned above can be attached to a suitable polymer by methods known in the art. In a preferred embodiment, the polymer support is polystyrene, for example, 1% cross-linked polystyrene-co-divinylbenzene with a HOBT loading of 1.02 mmol/g of polymer.

The precursor can be coupled to the polymer by using a suitable coupling agent or by using the combination of hexamethylphosphorus triamide (HMPT: $P(NMe_2)_3$) and iodine. Suitable coupling agents include BroP and PyBroP as defined in the abbreviations section above.

The reaction is conducted in a suitable solvent. Some examples of suitable solvents include $CH_2Cl_2$, $ClCH_2CH_2Cl$, and THF.

Isolation of the polymer and washing with a series of solvents yields the appropriate polymer-supported nucleosides. The polymer loading is in the range of 0.24–0.33 mmol/g.

Using the above procedure, compounds 22 and 23 were converted to polystyrene-supported $O^6$-(benzotriazol-1-yl)-3',5'-bis-O-(tert-butyldimethylsilyl)-2'-deoxyinosine (30) and polystyrene-supported $O^6$-(benzotriazol-1-yl)-2',3',5'-tris-O-(tert-butyldimethylsilyl)inosine (31) by coupling compounds 22 and 23 to 1-hydroxybenzotriazole-6-sulfonamidomethyl polystyrene (PS-HOBT).

Reaction Scheme 8
Synthesis of Polymer-supported convertible nucleoside derivatives.

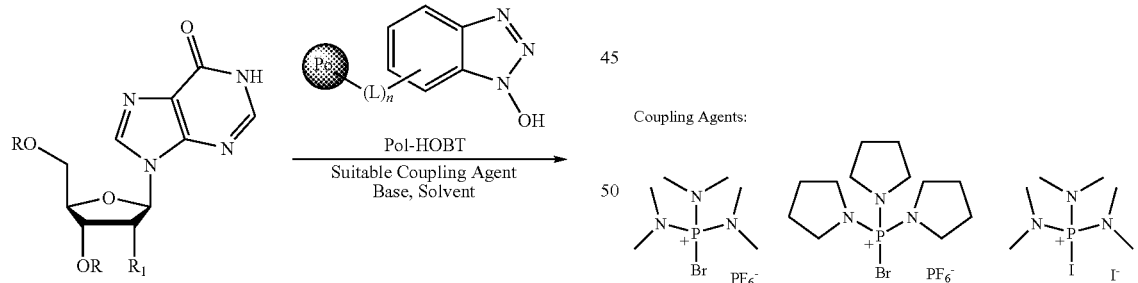

22: R = TBDMS, $R_1$ = H
23: R = TBDMS, $R_1$ = OTBDMS

-continued

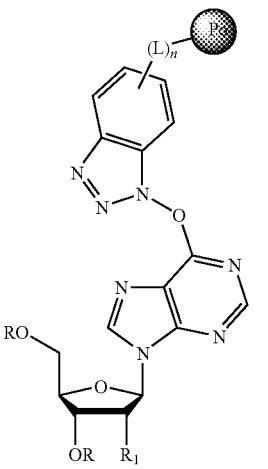

30: R = TBDMS, $R_1$ = H
31: R = TBDMS, $R_1$ = OTBDMS

Coupling Agents:

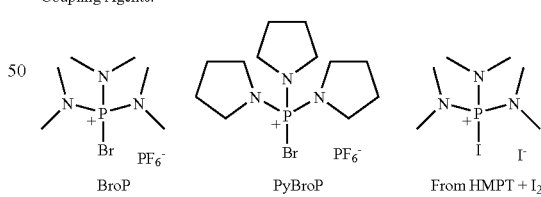

BroP    PyBroP    From HMPT + $I_2$

TABLE 2

Results of displacement reactions with convertible nucleoside derivates 22 and 23 and PS-HOBT.

| Entry | Polymer loading conditions (a, b) and cleavage (c) conditions | Product and yield[a] |
|---|---|---|
| 1 | a) BroP (5.0 molar eq), $Et_3N$ (5.0 molar eq), Pol-HOBT (1.0 molar eq), $CH_3CN$, rt (20 h)<br>b) 22 (2.0 molar eq), DIPEA (1.5 molar eq), THF, rt (65 h)<br>c) morpholine (1.7 molar eq), $Cs_2CO_3$ (1.7 molar eq), DME, rt (4 h)[a] | 11% |

TABLE 2-continued

Results of displacement reactions with convertible
nucleoside derivates 22 and 23 and PS-HOBT.

| Entry | Polymer loading conditions (a, b) and cleavage (c) conditions | Product and yield[a] |
|---|---|---|
| 2 | a) 22 (1.5 molar eq), BroP (1.0 molar eq), DIPEA (4.0 molar eq), CH$_2$Cl$_2$, rt (5 h)<br>b) Pol-HOBT (1.5 molar eq), rt (25 h)<br>c) morpholine (3.5 molar eq), Cs$_2$CO$_3$ (3.5 molar eq), DME, rt (4 h)[a] | 23% |
| 3 | a) 22 (1.0 molar eq), BroP (1.1 molar eq), DIPEA (4.0 molar eq), CH$_2$Cl$_2$, rt (7 h)<br>b) Pol-HOBT (1.5 molar eq), rt (24 h) and then 40° C. (30 h)<br>c) morpholine (2.8 molar eq), Cs$_2$CO$_3$ (2.0 molar eq), DME, rt (20 h)[a] | 58% |
| 4 | a) 22 (1.0 molar eq), BroP (1.1 molar eq), DIPEA (4.0 molar eq), THF, rt (7 h)<br>b) Pol-HOBT (1.5 molar eq), rt (17 h) and then 40° C. (30 h)<br>c) morpholine (2.8 molar eq), Cs$_2$CO$_3$ (2.0 molar eq), DME, rt (20 h)[a] | 65%[b] |
| 5 | a) 22 (1.0 molar eq), PyBroP (1.1 molar eq), DIPEA (4.0 molar eq), CH$_2$Cl$_2$, rt (17 h) | Not determined[c] |
| 6 | a) PPh$_3$ (3.0 molar eq), I$_2$ (3.0 molar eq), CH$_2$Cl$_2$, rt (30 min) and then 22 (1.0 molar eq), DIPEA (8.0 molar eq), rt (19 h)<br>b) Pol-HOBT (1.5 molar eq), rt (72 h) and then reflux (4 h)<br>c) morpholine (3.8 molar eq), DME, rt (23 h)[a] | 8% |
| 7 | a) HMPT (1.5 molar eq), I$_2$ (1.5 molar eq), CH$_2$Cl$_2$, rt (10 min) and then 22 (1.0 molar eq), DIPEA (4.0 molar eq), rt (2 h)<br>b) Pol-HOBT (1.5 molar eq), rt (22 h)<br>c) morpholine (2.0 molar eq), Cs$_2$CO$_3$ (2.0 molar eq), DME (1.0 mL), rt (20 h)[a] | 55% |
| 8 | a) HMPT (1.5 molar eq), I$_2$ (1.5 molar eq), CH$_2$Cl$_2$, rt (10 min) and then 23 (1.0 molar eq), DIPEA (4.0 molar eq), rt (1 h)<br>b) Pol-HOBT (1.5 molar eq), rt (22 h)<br>c) morpholine (2.0 molar eq), Cs$_2$CO$_3$ (2.0 molar eq), DME, rt (22 h)[a] | 58% |

[a]This step was performed to cleave the nucleoside from the polymer support. The yield of the resulting 6-morpholinyl nucleoside was used to estimate the efficiency of polymer loading.
[b]The resulting 6-morpholinyl product contained about 5% of an impurity (as assessed by $^1$H NMR).
[c]The reaction was significantly incomplete and about 48% 22 was left (as assessed by $^1$H NMR).

In Reaction Scheme 8, the polymer support is commercially available 1% cross-linked polystyrene-co-divinylbenzene with a HOBT loading of 1.02 mmol/g of polymer. After the reaction leading to attachment of the nucleoside to the polymer support, isolation of the polymer and washing with a series of solvents affords the appropriate polymer-supported nucleosides for further reactions. The polymer loading was in the range of 0.24-0.33 mmol/g as determined by cleavage of the nucleoside from the polymer support via the use of morpholine in the presence of Cs$_2$CO$_3$ in 1,2-dimethoxyethane.

The synthesis of polymer-bound HOBT has been reported in the literature. For example, see Pop, I. E.; Déprez, B. P.; Tartar, A. L. J. Org. Chem. 1997, 62, 2594-2603. There are various known methods for the attachment of HOBT to a polymer. See Kalir, R., Warshawsky, A., Fridkin, M., Patchornik, A. Eur. J. Biochem. 1975, 59, 55-61; Huang, W., Kalivretenos, A. G. Tetrahedron Lett. 1995, 36, 9113-9116; Dendrinos, K., Jeong, J., Huang, W., Kalivretenos, A. G. Chem. Commun. 1998, 499-500; Dendrinos, K. G., Kalivretenos, A. G. J. Chem. Soc., Perkin Trans. 1, 1998, 1463-1464; Dendrinos, K. G., Kalivretenos, A. G. Tetrahedron Lett. 1998, 39, 1321-1324; Chinchilla, R., Dodsworth, D. J., Nájera, C., Soriano, J. M. Tetrahedron Lett. 2000, 41, 2463-2466; and Scicinski, J. J., Congreve, M. S., Jamieson, C., Ley, S. V., Newman, E. S., Vinader, V. M., Carr, R. A. E. J. Combi. Chem. 2000, 3, 387-396.

In addition, polymer-bound HOBT is commercially available. For example, commercially available polymer-supported HOBT include

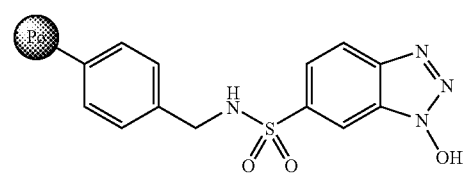

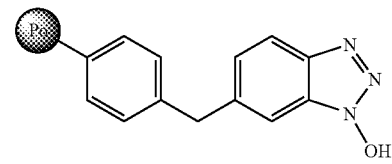

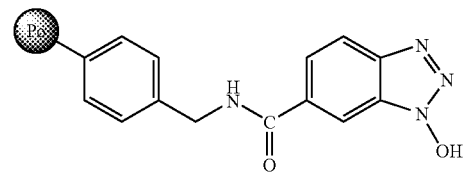

Any polymeric support can be attached to the HOBT entity if suitable starting materials for assembly of the HOBT core as well as complementary polymer supports are available. Some representative examples from the literature are shown below in Reaction Scheme 9.

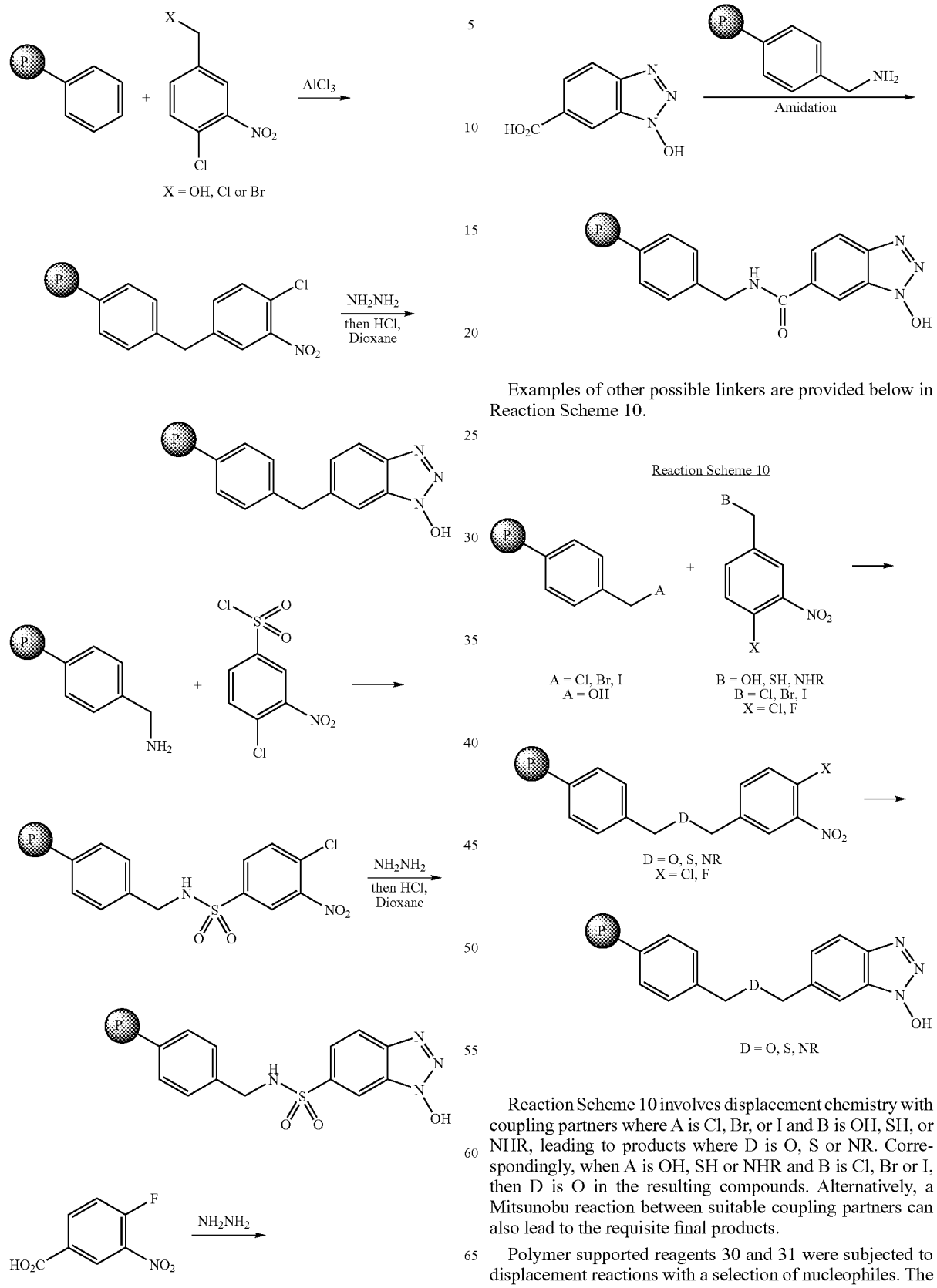

Examples of other possible linkers are provided below in Reaction Scheme 10.

Reaction Scheme 10 involves displacement chemistry with coupling partners where A is Cl, Br, or I and B is OH, SH, or NHR, leading to products where D is O, S or NR. Correspondingly, when A is OH, SH or NHR and B is Cl, Br or I, then D is O in the resulting compounds. Alternatively, a Mitsunobu reaction between suitable coupling partners can also lead to the requisite final products.

Polymer supported reagents 30 and 31 were subjected to displacement reactions with a selection of nucleophiles. The results from these reactions are collected in Table 3 below.

TABLE 3

Reaction of polymer-supported nucleosides with nucleophiles

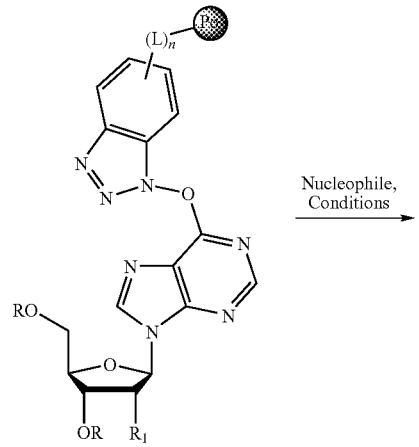

30: R = TBDMS, R$_1$ = H
31: R = TBDMS, R$_1$ = OTBDMS

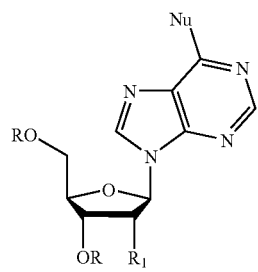

| Entry | Compound | Nucleophile | Condition | Product, yield |
|---|---|---|---|---|
| 1 | 30 | CH$_3$OH | CH$_3$OH, Cs$_2$CO$_3$, rt, 24 h | 91% |
| 2 | 30 | CH$_3$CH$_2$OH | CH$_3$CH$_2$OH, Cs$_2$CO$_3$, rt, 36 h | 51% |
|   |    |                | CH$_3$CH$_2$OH, Cs$_2$CO$_3$, 78° C., 15 h | 87% |
| 3 | 30 | (CH$_3$)$_2$CHOH | (CH$_3$)$_2$OH, Cs$_2$CO$_3$, 82° C., 15 h | No reaction |
| 4 | 30 | phenol | DME, Cs$_2$CO$_3$, 85° C., 1 h | 41%$^a$ |
| 5 | 30 | 4-nitrophenol | DME, Cs$_2$CO$_3$, 85° C., 15 h | 54% |
| 6 | 30 | 3-cyanophenol | DME, Cs$_2$CO$_3$, 85° C., 15 h | 68% |
| 7 | 30 | 1-naphthol | DME, Cs$_2$CO$_3$, 85° C, 15 h | 49%$^a$ |

TABLE 3-continued

| # | | Reagent | Conditions | Yield |
|---|---|---|---|---|
| 8 | 30 | 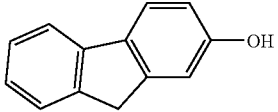 [SMILES: Oc1ccc2c(c1)Cc1ccccc1-2] | DME, Cs$_2$CO$_3$, 85° C., 8 h | 39%[a] |
| 9 | 30<br>31 | 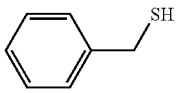 | DME, Cs$_2$CO$_3$, rt (24 h)<br>and then 85° C. (20 h)<br>DME, Cs$_2$CO$_3$, rt, 24 h | 87%[a]<br>46%[a] |
| 10 | 30<br>31 | (CH$_3$)$_2$NH | DME, rt, 24 h<br>DME, rt, 24 h | quantitative<br>quantitative |
| 11 | 30 |  | DME, rt, 24 h | quantitative |
| 12 | 30<br>31 | 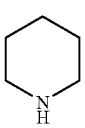 | DME, rt, 24 h<br>DME, rt, 24 h | quantitative<br>quantitative |
| 13 | 30<br>30<br>30<br>30<br>31 | 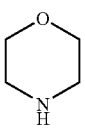 | DME, Cs$_2$CO$_3$, rt, 34 h<br>DME, Cs$_2$CO$_3$, 85° C., 15 h<br>CH$_2$Cl$_2$, Cs$_2$CO$_3$, rt, 34 h<br>DME, rt, 24 h<br>DME, rt, 24 h | quantitative<br>quantitative<br>95%<br>quantitative<br>quantitative |
| 14 | 30 | 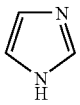 | DME, Cs$_2$CO$_3$, 85° C., 15 h | 69% |
| 15 | 30<br>31 | 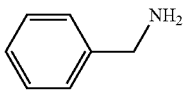 | DME, rt, 24 h<br>DME, rt, 24 h | quantitative<br>92% |

[a]Product formation in these cases is accompanied by 8-31% of 32i as seen in the $^1$H NMR or by TLC analysis of the crude reaction products.

Uses of Convertible Nucleoside Derivatives

Convertible nucleosides provide a facile approach to the synthesis of modified nucleosides that are useful for biochemical and biological studies. For example, convertible nucleoside derivatives can be incorporated into DNA. In such a case, the nucleoside may, for example, be labeled. See Example 36.

In another utility, convertible nucleosides can also be used to synthesize 1,N$^6$-ethano- and 1,N$^6$-propano-2'-deoxyadenosine analogues. Alkylating nitrosoureas as a class are used in the chemotherapy of solid tumors and leukemias. Among these, 1,3-bis(2-chloroethyl)-1-nitrosourea (BCNU, carmustine) is a potent analogue for the treatment of brain tumors. The DNA cross-linking properties of 2-chloroethyl-1-nitrosoureas are associated with their cell lethality. However, the reaction of BCNU with DNA results in a variety of other alkylation products, one of which is 1,N$^6$-ethano-2'-deoxyadenosine. This compound is related to the 1,N$^6$-ethenoadenine derivatives that are formed from the reaction of vinyl chloride with 9-methyladenine or adenosine. Since the hydrogen bonding sites of 2'-deoxyadenosine are directly involved in the ring formation, synthetic access to 1,N$^6$-ethano-2'-deoxyadenosine is useful to understand its biological consequences. See Example 37.

EXAMPLES

The specific examples describe a preferred method for synthesizing the compounds of the present invention. The scope of this invention is not to be in any way limited by the examples set forth herein.

Reactions were monitored by TLC (silica gel, 250 μm) and column chromatographic purifications were performed on 200-300 mesh silica gel. Solvents used for eluting the compounds, as well as TLC conditions and R$_f$ values, are provided under individual compound headings. All other reagents were obtained from commercial sources and used without further purification. $^1$H NMR spectra were recorded at 500 MHz and $^{13}$C NMR were recorded at 126 MHz. $^{31}$P NMR spectra (202 MHz) were referenced to 85% H$_3$PO$_4$ as an external standard. All spectra were appropriately referenced. Chemical shifts are reported in δ parts per million, and coupling constants are in hertz. The sugar protons are numbered 1'-5' beginning at the anomeric carbon and proceeding via the carbon chain to the primary carbinol carbon.

Example 1

Synthesis of 9-(2-Deoxy-3,5-bis-O-(tert-butyldimethylsilyl)-β-D-erythro-pentofuranosyl)purin-6-yloxy-(tris(dimethylamino)phosphonium)hexafluorophosphate

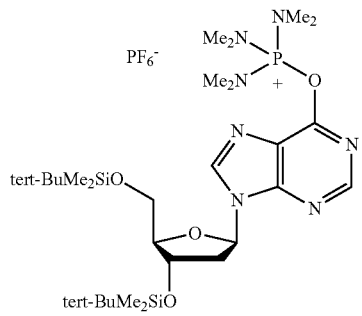

In a clean, dry reaction vial equipped with a stirring bar were placed 3',5'-bis-O-(tert-butyldimethylsilyl)-2'-deoxyinosine (23) (0.100 g, 0.208 mmol) and BOP (0.184 g, 0.416 mmol). Dry THF (2.0 mL) and DIPEA (54.3 μL, 0.312 mmol) were added and the mixture was allowed to stir at room temperature for 4 h and then evaporated. The crude material was taken up in $CH_2Cl_2$ and washed with water. The organic layer was separated, dried over $Na_2SO_4$ and concentrated. Purification by preparative thin layer chromatography ($SiO_2$, 5% MeOH in $CH_2Cl_2$) afforded ~10 mg (6% yield) of the product as a clear gum. $R_f$(5% MeOH in $CH_2Cl_2$)=0.26. $^1$H NMR (500 MHz, $CDCl_3$): δ 8.68 (s, 1H, Ar—H), 6.54 (t, 1H, H-1', J=6.4), 4.63 (m, 1H, H-3'), 4.06 (q, 1H, H-4', J=3.3), 3.89 (dd, 1H, H-5', J=11.2, 3.7), 3.79 (dd, 1H, H-5', J=11.2, 2.9), 2.66 (app quint, 1H, H-2', $J_{app}$~6.4), 2.52 (ddd, 1H, H-2', J=13.2, 5.9, 3.9), 2.92 (d, 18H, $NCH_3$, $J_{H—P}$=11.2), 0.92, 0.90 (2 s, 18H, tert-Bu), 0.11, 0.09, 0.08 (3 s, 12H, $SiCH_3$). $^{13}$C NMR (126 MHz, $CDCl_3$): δ 154.4, 152.7, 151.5, 144.5, 123.0, 88.4, 85.2, 71.9, 62.7, 41.4, 37.3 (d, $J_{C—P}$=4.5), 25.9, 25.7, 18.4, 18.0, −4.7, −4.8, −5.4, −5.5. $^{31}$P NMR (202 MHz, $CDCl_3$): δ 35.44 (s, P[N($CH_3$)$_2$]$_3$), −143.31 (septet, $PF_6$, $J_{P,F}$=712).

Example 2

Synthesis of $O^6$-(Benzotriazol-1-yl)-3',5'-bis-O-(tert-butyldimethylsilyl)-2'-deoxyinosine (26)

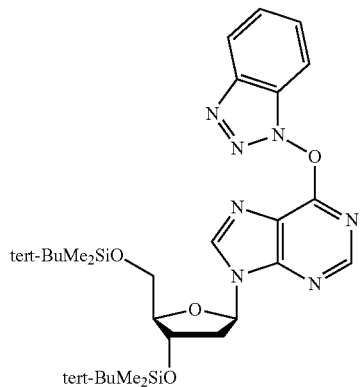

In a 50 mL round-bottomed flask equipped with a stirring bar were placed 3',5'-bis-O-(tert-butyldimethylsilyl)-2'-deoxyinosine (22) (1.005 g, 2.090 mmol) and BOP (1.850 g, 4.181 mmol). THF (20 mL) and DIPEA (0.55 mL, 3.135 mmol) were added and the mixture was allowed stir at room temperature for 23 h. The mixture was evaporated and $CH_2Cl_2$ (50 mL) added. The mixture was washed with water, dried over $Na_2SO_4$ and concentrated. Chromatographic purification ($SiO_2$, elution with 20% EtOAc in hexanes) afforded 1.038 g (83% yield) of compound 26 as a white foam. $R_f$(20% EtOAc in hexanes)=0.14. $^1$H NMR (500 MHz, $CDCl_3$): δ 8.54 (s, 1H, Ar—H), 8.41 (s, 1H, Ar—H), 8.14 (d, 1H, Ar—H, J=8.3), 7.55-7.41 (m, 3H, Ar—H), 6.55 (t, 1H, H-1', J=6.1), 4.65 (m, 1H, H-3'), 4.06 (q, 1H, H-4', J=3.1), 3.92 (dd, 1H, H-5', J=11.2, 3.9), 3.80 (dd, 1H, H-5', J=11.2, 2.7), 2.65 (app quint, 1H, H-2', $J_{app}$~6.3), 2.52 (m, 1H, H-2'), 0.93, 0.92 (2 s, 18H, tert-Bu), 0.11 (s, 12H, $SiCH_3$). $^{13}$C NMR (126 MHz, $CDCl_3$): δ 159.0, 153.6, 151.3, 143.5, 128.9, 128.7, 124.8, 120.6, 120.0, 108.6, 88.2, 85.0, 71.6, 62.6, 41.7, 25.9, 25.7, 18.4, 18.0, −4.7, −4.8, −5.4, −5.5. FAB HRMS calcd for $C_{28}H_{44}N_7O_4Si_2$ ($M^+$+H) 598.2993. found 598.2986.

Alternate Synthesis of $O^6$-(Benzotriazol-1-yl)-3',5'-bis-O-(tert-butyldimethylsilyl)-2'-deoxyinosine (26)

In a 50 mL round-bottom flask equipped with a stirring bar were placed $PPh_3$ (0.823 g, 3.138 mmol) and $I_2$ (0.800 g, 3.152 mmol) in dry $CH_2Cl_2$ (11.0 mL) and the mixture was stirred at room temperature for 20 min. DIPEA (1.5 mL, 8.62 mmol) and 3',5'-bis-O-(tert-butyldimethylsilyl)-2'-deoxyinosine (1a) (0.500 g, 1.040 mmol) were added, and the mixture was allowed to stir at room temperature for 26 h. To this mixture was added HOBT (0.211 g, 1.561 mmol) and the reaction was allowed to continue and was complete in 22 h. The crude material was evaporated and chromatographic purification ($SiO_2$, elution with 20% EtOAc in hexanes) afforded 0.578 g (93%) of compound 26 as a beige foam.

Example 2a

Synthesis of $O^6$-(Triazolyl-1-yl)-3',5'-bis-O-(tert-butyldimethylsilyl)-2'-deoxyinosine (26a)

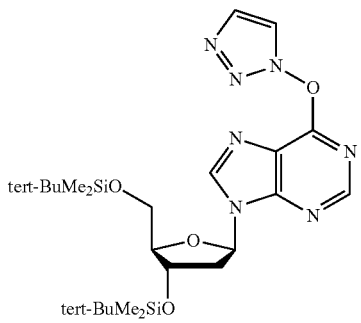

In a 50 mL round-bottomed flask equipped with a stirring bar are placed 3',5'-bis-O-(tert-butyldimethylsilyl)-2'-deoxyinosine (22) and triazolyl-1-yloxy-tris(dimethylamino)phosphonium. THF and DIPEA are added and the mixture is stirred at room temperature for 23 h. The mixture is evaporated and $CH_2Cl_2$ (50 mL) is added. The mixture is washed with water. Then the mixture is dried over $Na_2SO_4$. Finally, the mixture is concentrated.

Example 2b

Synthesis of O⁶-(Imidazolyl-1-yl)-3',5'-bis-O-(tert-butyldimethylsilyl)-2'-deoxyinosine (26b)

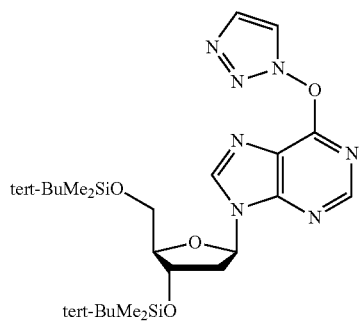

In a 50 mL round-bottomed flask equipped with a stirring bar are placed 3',5'-bis-O-(tert-butyldimethylsilyl)-2'-deoxyinosine (22) and imidazolyl-1-yloxy-tris(dimethylamino)phosphonium. THF and DIPEA are added and the mixture is stirred at room temperature for 23 h. The mixture is evaporated and $CH_2Cl_2$ (50 mL) is added. The mixture is washed with water. Then the mixture is dried over $Na_2SO_4$. Finally, the mixture is concentrated.

Example 3

Synthesis of O⁶-(Benzotriazol-1-yl)-2',3',5'-tris-O-(tert-butyldimethylsilyl)inosine (27)

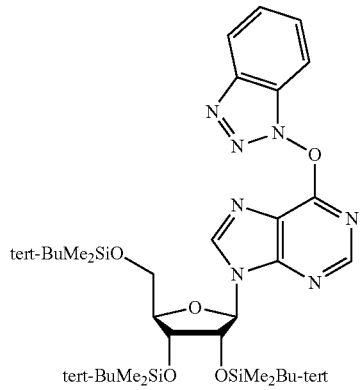

As described for the synthesis of 26, 27 was prepared by a reaction between 2',3',5'-tris-O-(tert-butyldimethylsilyl) inosine (23) (3.055 g, 5.00 mmol), BOP (4.425 g, 10.0 mmol) and DIPEA (1.31 mL, 7.5 mmol) in dry THF (50.0 mL). Chromatographic purification ($SiO_2$, elution with 20% EtOAc in hexanes) afforded 2.898 g (80% yield) of compound 27 as a white, foamy solid. $R_f$ (20% EtOAc in hexanes)=0.32. ¹H NMR (500 MHz, $CDCl_3$): δ 8.63 (s, 1H, Ar—H), 8.40 (s, 1H, Ar—H), 8.15 (d, 1H, Ar—H, J=8.3), 7.56-7.45 (m, 3H, Ar—H), 6.16 (d, 1H, H-1', J=4.4), 4.58 (t, 1H; H-2', J=4.4), 4.34 (t, 1H, H-3', J=4.2), 4.18 (app q, 1H, H-4', $J_{app}$~3.1), 4.06 (dd, 1H, H-5', J=11.7, 3.4), 3.82 (dd, 1H, H-5', J=11.7, 2.4), 0.98, 0.94, 0.82 (3 s, 27H, tert-Bu), 0.17, 0.16, 0.11, 0.10, 0.0, −0.17 (6 s, 18H, $SiCH_3$). ¹³C NMR (126 MHz, $CDCl_3$): δ 159.0, 153.9, 151.4, 143.9, 143.5, 129.0, 128.7, 124.8, 120.6, 120.0, 108.6, 88.9, 85.5, 76.4, 71.6, 62.2, 26.1, 25.8, 25.6, 18.5, 18.0, 17.8, −4.4, −4.7, −4.73, −5.0, −5.3, −5.4. FAB HRMS calcd for $C_{34}H_{58}N_7O_5Si_3$ (M⁺+H) 728.3807. found 728.3818.

Alternate Synthesis of O⁶-(Benzotriazol-1-yl)-2',3',5'-tris-O-(tert-butyldimethylsilyl)inosine (27)

As described for the synthesis of O⁶-(benzotriazol-1-yl)-3',5'-bis-O-(tert-butyldimethylsilyl)-2'-deoxyinosine, this ribose derivative was prepared by a reaction of $PPh_3$ (0.645 g, 2.459 mmol), $I_2$ (0.632 g, 2.490 mmol), DIPEA (1.2 mL, 6.89 mmol), 2',3',5'-tris-O-(tert-butyldimethylsilyl)inosine (1b) (0.500 g, 0.818 mmol) and HOBT (0.166 g, 1.228 mmol) in dry $CH_2Cl_2$ (9.0 mL). Chromatographic purification ($SiO_2$, elution with 20% EtOAc in hexanes) afforded 0.537 g (90%) of compound 4b as a yellowish-white foam.

Example 4

Synthesis of O⁶-(Benzotriazol-1-yl)-2'-deoxyinosine (28)

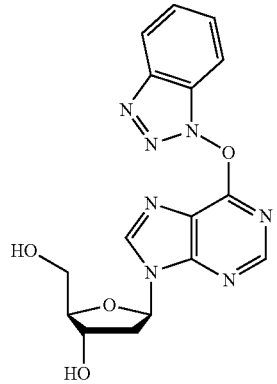

In a 50 mL round-bottomed flask equipped with a stirring bar were placed 2'-deoxyinosine 24 (0.504 g, 2.00 mmol) and BOP (1.770 g, 4.00 mmol). DMF (20 mL) and DIPEA (0.70 mL, 4.00 mmol) were added and the mixture was allowed to stir at room temperature for 26 h. The reaction mixture was evaporated with toluene several times. The crude product was dissolved in EtOAc and washed with water. The organic layer was separated, dried over $Na_2SO_4$ and concentrated. Chromatographic purification ($SiO_2$, elution with 10% MeOH in $CH_2Cl_2$) afforded 0.421 g (57% yield) of compound 28 as a pale brownish-white foam. $R_f$ (10% MeOH in $CH_2Cl_2$)=0.38. ¹H NMR (500 MHz, $CDCl_3$): δ 8.43 (s, 1H, Ar—H), 8.24 (s, 1H, Ar—H), 8.16-8.14 (m, 1H, Ar—H), 7.57-7.54 (m, 1H, Ar—H), 7.49-7.46 (m, 1H, Ar—H), 6.46 (dd, 1H, H-1', J=9.2, 5.5), 5.10 (dd, 1H, OH, J=11.3, 2.3, $CD_3OD$ exchangeable), 4.83 (br m, 1H, H-3'), 4.25 (br s, 1H, H-4'), 3.97 (dt, 1H, H-5', J=12.8, 2.0), 3.82 (app td, 1H, H-5', $J_{app}$~11.9, 1.8), 3.07 (ddd, 1H, H-2', J=13.4, 9.5, 4.9), 2.42 (dd, 1H, H-2', J=13.6, 5.7), 2.05 (d, 1H, OH, $CD_3OD$ exchangeable). ¹³C NMR (126 MHz, DMSO-$d_6$): δ 159.1, 153.1, 151.1, 144.8, 143.2, 129.1, 128.8, 125.2, 120.5, 120.3, 108.7, 88.9, 86.9, 72.2, 62.7, 40.9. FAB HRMS calcd for $C_{16}H_{16}N_7O_4$ (M⁺+H) 370.1264. found 370.1258.

Example 5

Synthesis of O⁶-(Benzotriazol-1-yl)inosine (29)

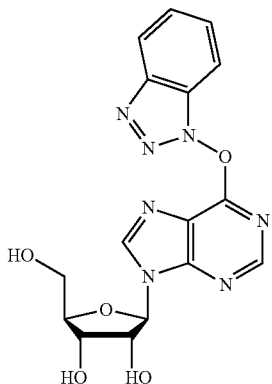

In a reaction vial equipped with a stirring bar were placed inosine 25 (0.100 g, 0.373 mmol) and BOP (0.330 g, 0.746 mmol). DMF (3.7 mL) and DIPEA (97.3 μL, 0.559 mmol) were added, the reaction vial was flushed with $N_2$ and the mixture allowed to stir at room temperature for 68 h. To the reaction mixture water was added and the mixture was extracted with $CH_2Cl_2$. The organic layer was separated, washed with brine, dried over $Na_2SO_4$ and concentrated. Since the crude product contained residual DMF, toluene was added and evaporated several times. Chromatographic purification ($SiO_2$, elution with 5% MeOH in $CH_2Cl_2$) afforded 76 mg (53% yield) of 29 as a white powder. $R_f$ (5% MeOH in $CH_2Cl_2$)=0.09. $^1$H NMR (500 MHz, DMSO-$d_6$): δ 8.95 (s, 1H, Ar—H), 8.53 (s, 1H, Ar—H), 8.21 (d, 1H, Ar—H, J=8.8), 7.80 (d, 1H, Ar—H, J=8.3), 7.66 (t, 1H, Ar—H, J=7.6), 7.56 (t, 1H, Ar—H, J=7.6), 6.09 (d, 1H, H-1', J=5.4), 5.55 (d, 1H, OH, J=5.9, $D_2O$ exchangeable), 5.24 (d, 1H, OH, J=5.4, $D_2O$ exchangeable), 5.07 (t, 1H, OH, J=5.6, $D_2O$ exchangeable), 4.62 (q, 1H, H-2', J=5.4), 4.21 (q, 1H, H-3', J=4.7), 4.01 (m, 1H, H-4'), 3.71 (m, 1H, H-5'), 3.60 (m, 1H, H-5'). $^{13}$C NMR (126 MHz, DMSO-$d_6$): δ 159.0, 154.8, 151.9, 146.1, 143.5, 130.1, 129.3, 126.1, 120.7, 119.8, 110.2, 88.9, 86.5, 74.7, 70.9, 61.8. FAB HRMS calcd for $C_{16}H_{16}N_7O_5$ (M⁺+H) 386.1213. found 386.1191.

Example 6

Synthesis of 3',5'-Bis-O-(tert-butyldimethylsilyl)-O⁶-methyl-2'-deoxyinosine

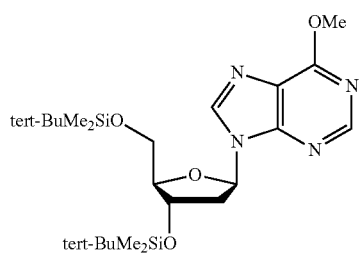

In a clean, dry reaction vial equipped with a stirring bar were placed O⁶-(benzotriazol-1-yl)-3',5'-bis-O-(tert-butyldimethylsilyl)-2'-deoxyinosine (26) (59.8 mg, 0.100 mmol), $Cs_2CO_3$ (65.2 mg, 0.200 mmol) and methanol (1.0 mL). The reaction mixture was flushed with $N_2$ and stirred at room temperature for 1 h after which the mixture was evaporated to dryness. Chromatographic purification ($SiO_2$, elution with 20% EtOAc in hexanes) afforded 38 mg (77% yield) of the title compound as a clear gum. $R_f$ (20% EtOAc in hexanes)=0.12. $^1$H NMR (500 MHz, CDCl₃): δ 8.52 (s, 1H, Ar—H), 8.27 (s, 1H, Ar—H), 6.49 (t, 1H, H-1', J=6.3), 4.62 (m, 1H, H-3'), 4.18 (s, 3H, OCH₃), 4.01 (q, 1H, H-4', J=3.4), 3.87 (dd, 1H, H-5', J=11.2, 3.9), 3.77 (dd, 1H, H-5', J=11.2, 2.9), 2.62 (app quint, 1H, H-2', $J_{app}$~6.3), 2.45 (ddd, 1H, H-2', J=13.2, 6.4, 3.9), 0.91 (s, 18H, tert-Bu), 0.09, 0.08 (2 s, 12H, SiCH₃). $^{13}$C NMR (126 MHz, CDCl₃): δ 161.1, 152.0, 151.5, 140.6, 122.0, 88.0, 84.5, 71.9, 62.8, 54.0, 41.4, 25.9, 25.7, 18.4, 17.9, −4.7, −4.8, −5.5, −5.6. FAB HRMS calcd for $C_{23}H_{43}N_4O_4Si_2$ (M⁺+H) 495.2823. found 495.2798.

Example 7

Synthesis of 3',5'-Bis-O-(tert-butyldimethylsilyl)-O⁶-ethyl-2'-deoxyinosine

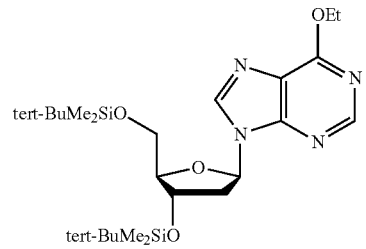

As described for the synthesis of 3',5'-bis-O-(tert-butyldimethylsilyl)-O⁶-methyl-2'-deoxyinosine, the ethyl derivative was prepared by a reaction between O⁶-(benzotriazol-1-yl)-3',5'-bis-O-(tert-butyldimethylsilyl)-2'-deoxyinosine (26) (59.8 mg, 0.100 mmol) and EtOH (1 mL) in the presence of $Cs_2CO_3$ (65.2 mg, 0.200 mmol) over 1 h. Chromatographic purification ($SiO_2$, elution with 20% EtOAc in hexanes) afforded 48.2 mg (95% yield) of the title compound as a clear gum. $R_f$ (20% EtOAc in hexanes)=0.16. $^1$H NMR (500 MHz, CDCl₃): δ 8.50 (s, 1H, Ar—H), 8.26 (s, 1H, Ar—H), 6.50 (t, 1H, H-1', J=6.4), 4.65 (q, 2H, OCH₂, J=7.0), 4.61 (m, 1H, H-3'), 4.01 (q, 1H, H-4', J=3.4), 3.87 (dd, 1H, H-5', J=11.2, 3.9), 3.77 (dd, 1H, H-5', J=11.2, 2.9), 2.61 (quint, 1H, H-2', J=6.3), 2.44 (ddd, 1H, H-2', J=12.9, 6.1, 3.9), 1.50 (t, 3H, CH₃, J=7.3), 0.91 (s, 18H, tert-Bu), 0.09, 0.08 (2 s, 12H, SiCH₃). $^{13}$C NMR (126 MHz, CDCl₃): δ 160.8, 152.0, 151.5, 140.5, 121.9, 87.9, 84.4, 71.8, 63.1, 62.7, 41.5, 26.0, 25.7, 18.4, 18.0, 14.5, −4.7, −4.8, −5.4, −5.5. FAB HRMS calcd for $C_{24}H_{45}N_4O_4Si_2$ (M⁺+H) 509.2979. found 509.2953.

Example 8

Synthesis of 3',5'-Bis-O-(tert-butyldimethylsilyl)-O⁶-isopropyl-2'-deoxyinosine

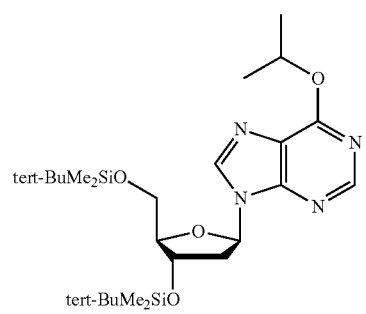

As described for the synthesis of 3',5'-bis-O-(tert-butyldimethylsilyl)-O⁶-methyl-2'-deoxyinosine, the isopropyl derivative was prepared by a reaction between O⁶-(benzotriazol-1-yl)-3',5'-bis-O-(tert-butyldimethylsilyl)-2'-deoxyinosine (26) (59.8 mg, 0.100 mmol) and 2-propanol (1 mL) in the presence of Cs$_2$CO$_3$ (65.2 mg, 0.200 mmol) over 10 h. Chromatographic purification (SiO$_2$, elution with 20% EtOAc in hexanes) afforded 44.1 mg (84% yield) of the title compound as a clear gum. R$_f$ (20% EtOAc in hexanes)=0.31. ¹H NMR (500 MHz, CDCl$_3$): δ 8.50 (s, 1H, Ar—H), 8.23 (s, 1H, Ar—H), 6.49 (t, 1H, H-1', J=6.3), 5.67 (septet, 1H, —CH—, J=6.3), 4.61 (m, 1H, H-3'), 4.02 (m, 1H, H-4'), 3.87 (dd, 1H, H-5', J=11.2, 3.9), 3.78 (dd, 1H, H-5', J=10.7, 2.9), 2.63 (app quint, 1H, H-2', J$_{app}$~6.3), 2.44 (ddd, 1H, H-2', J=13.2, 5.9, 3.9), 1.47 (d, 6H, CH$_3$, J=6.5), 0.91 (s, 18H, tert-Bu), 0.10, 0.09 (2 s, 12H, SiCH$_3$). ¹³C NMR (126 MHz, CDCl$_3$): δ 160.5, 152.0, 151.5, 140.3, 122.0, 87.9, 84.4, 71.9, 71.2, 62.8, 41.4, 26.0, 25.7, 22.0, 18.4, 18.0, −4.7, −4.8, −5.4, −5.5. FAB HRMS calcd for C$_{25}$H$_{47}$N$_4$O$_4$Si$_2$ (M⁺+H) 523.3136. found 523.3130.

Example 9

Synthesis of O⁶-Isopropyl-2',3',5'-tris-O-(tert-butyldimethylsilyl)inosine

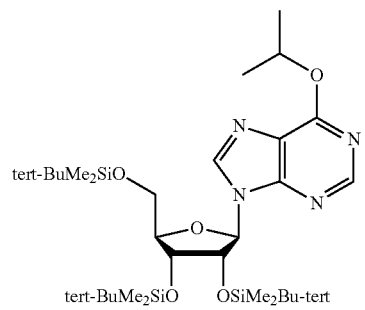

As described for the synthesis of 3',5% bis-O-(tert-butyldimethylsilyl)-O⁶-methyl-2'-deoxyinosine, this isopropyl derivative was prepared by a reaction between O⁶-(benzotriazol-1-yl)-2',3',5'-tris-O-(tert-butyldimethylsilyl)-2'-deoxyinosine (27) (71.8 mg, 0.099 mmol) and 2-propanol (1 mL) in the presence of Cs$_2$CO$_3$ (65.2 mg, 0.200 mmol) over 24 h at room temperature and then at 85° C. for 3 h. Chromatographic purification (SiO$_2$, elution with 20% EtOAc in hexanes) afforded 45.6 mg (70% yield) of the title compound as a clear gum. R$_f$ (20% EtOAc in hexanes)=0.59. ¹H NMR (500 MHz, CDCl$_3$): δ 8.49 (s, 1H, Ar—H), 8.27 (s, 1H, Ar—H), 6.08 (d, 1H, H-1', J=5.4), 5.66 (septet, 1H, —CH—, J=6.3), 4.64 (t, 1H, H-2', J=4.6), 4.32 (t, 1H, H-3', J=3.9), 4.13 (q, 1H, H-4', J=3.3), 4.02 (dd, 1H, H-5', J=11.2, 3.9), 3.79 (dd, 1H, H-5', J=11.2, 2.7), 1.48 (d, 3H, CH$_3$, J=6.4), 1.47 (d, 3H, CH$_3$, J=6.4), 0.95, 0.93, 0.79 (3 s, 27H, tert-Bu), 0.14, 0.13, 0.10, 0.09, −0.05, −0.23 (6 s, 18H, SiCH$_3$). ¹³C NMR (126 MHz, CDCl$_1$): δ160.5, 152.0, 151.9, 140.8, 122.1, 88.3, 85.4, 76.0, 71.9, 70.2, 62.5, 26.1, 25.8, 25.6, 22.0, 18.5, 18.1, 17.8, −4.4, −4.7, −4.73, −5.1, −5.4. FAB HRMS calcd for C$_{31}$H$_{61}$N$_4$O$_5$Si$_3$ (M⁺+H) 653.3950. found 653.3944.

Example 10

Synthesis of O⁶-Allyl-3',5'-bis-O-(tert-butyldimethylsilyl)-2'-deoxyinosine

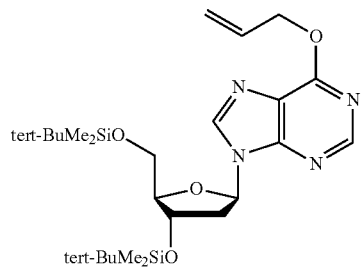

As described for the synthesis of 3',5-bis-O-(tert-butyldimethylsilyl)-O⁶-methyl-2'-deoxyinosine, the allyl derivative was prepared by a reaction between O⁶-(benzotriazol-1-yl)-3',5-bis-O-(tert-butyldimethylsilyl)-2'-deoxyinosine (26) (59.8 mg, 0.100 mmol) and allyl alcohol (1 mL) in the presence of Cs$_2$CO$_3$ (65.2 mg, 0.200 mmol) over 2 h. Chromatographic purification (SiO$_2$, elution with 20% EtOAc in hexanes) afforded 46.4 mg (89% yield) of the title compound as a clear gum. R$_f$ (20% EtOAc in hexanes)=0.29. ¹H NMR (500 MHz, CDCl$_3$): δ 8.51 (s, 1H, Ar—H), 8.27 (s, 1H, Ar—H), 6.50 (t, 1H, H-1', J=6.4), 6.16 (m, 1H, —CH=), 5.45 (dd, 1H, =CH$_{trans}$, J=17.1, 1.5), 5.29 (d, 1H, =CH$_{cis}$, J=10.7), 5.12 (d, 2H, OCH$_2$, J=5.4), 4.61 (m, 1H, H-3'), 4.02 (q, 1H, H-4', J=3.4), 3.87 (dd, 1H, H-5', J=11.2, 3.9), 3.77 (dd, 1H, H-5', J=11.2, 2.9), 2.61 (app quint, 1H, H-2', J$_{app}$~6.3), 2.44 (ddd, 1H, H-2', J=12.9, 6.1, 3.9), 0.91 (s, 18H, tert-Bu), 0.09, 0.08 (2 s, 12H, SiCH$_3$). ¹³C NMR (126 MHz, CDCl$_3$): δ 160.3, 151.9, 151.6, 140.6, 132.4, 121.9, 118.5, 87.9, 84.4, 71.8, 67.5, 62.7, 41.4, 26.0, 25.7, 18.4, 18.0, −4.7, −4.8, −5.4, −5.5. FAB HRMS calcd for C$_{25}$H$_{45}$N$_4$O$_4$Si$_2$ (M⁺+H) 521.2979. found 521.2974.

Example 11

Synthesis of 3',5'-Bis-O-(tert-butyldimethylsilyl)-O⁶-phenyl-2'-deoxyinosine

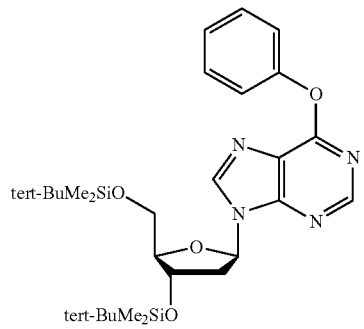

In a clean, dry reaction vial equipped with a stirring bar were placed O⁶-(benzotriazol-1-yl)-3',5'-bis-O-(tert-butyldimethylsilyl)-2'-deoxyinosine (26) (63.2 mg, 0.106 mmol), Cs$_2$CO$_3$ (68.9 mg, 0.211 mmol) and phenol (19.9 mg, 0.211 mmol). Dry toluene (1.0 mL) was added and the reaction mixture was flushed with N$_2$ and the mixture was allowed to stir at 105° C. for 2 h. The reaction mixture was filtered through Celite, the residue washed with Et$_2$O and the filtrate evaporated to dryness. Chromatographic purification (SiO$_2$, elution with 20% EtOAc in hexanes) afforded 50.5 mg (86% yield) of the title compound as a clear gum. R$_f$(20% EtOAc in hexanes)=0.21. $^1$H NMR (500 MHz, CDCl$_3$): δ 8.49 (s, 1H, Ar—H), 8.40 (s, 1H, Ar—H), 7.45 (app t, 2H, Ar—H, J$_{app}$~7.8), 7.29-7.26 (m, 3H, Ar—H), 6.53 (t, 1H, H-1', J=6.3), 4.64 (m, 1H, H-3'), 4.04 (q, 1H, H-4', J=3.4), 3.90 (dd, 1H, H-5', J=11.2, 3.9), 3.70 (dd, 1H, H-5', J=11.2, 2.7), 2.65 (app quint, 1H, H-2', J$_{app}$~6.3), 2.48 (ddd, 1H, H-2', J=13.2, 6.1, 4.1), 0.92, 0.91 (2 s, 18H, tert-Bu), 0.10 (s, 12H, SiCH$_3$). $^{13}$C NMR (126 MHz, CDCl$_3$): δ 160.2, 152.5, 152.4, 152.0, 141.6, 129.6, 125.7, 122.1, 121.9, 88.0, 84.6, 71.8, 62.7, 41.5, 26.0, 25.7, 18.4, 18.0, −4.7, −4.8, −5.4, −5.5. FAB HRMS calcd for C$_{28}$H$_{45}$N$_4$O$_4$Si$_2$ (M$^+$+H) 557.2979. found 557.2978.

Example 12

Synthesis of 3',5-Bis-O-(tert-butyldimethylsilyl)-O$^6$-(4-nitrophenyl)-2'-deoxyinosine

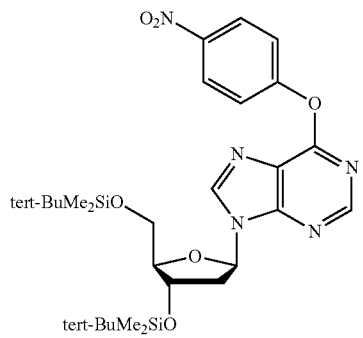

In a clean, dry reaction vial equipped with a stirring bar were placed O$^6$-(benzotriazol-1-yl)-3',5'-bis-O-(tert-butyldimethylsilyl)-2'-deoxyinosine (26) (40 mg, 0.067 mmol), Cs$_2$CO$_3$ (43.6 mg, 0.134 mmol) and 4-nitrophenol (18.6 mg, 0.134 mmol). Dry DME (0.7 mL) was added and the reaction mixture was flushed with N$_2$ and the mixture was allowed to stir at 85° C. for 2 h. The reaction mixture was diluted with EtOAc and washed with 0.1 N aq NaOH followed by brine. The organic layer was dried over Na$_2$SO$_4$, and evaporated to dryness. Chromatographic purification (SiO$_2$, elution with 50% EtOAc in hexanes) afforded 31.3 mg (78% yield) of the title compound as a yellow gum. R$_f$(5% MeOH in CH$_2$Cl$_2$)= 0.58. $^1$H NMR (500 MHz, CDCl$_3$): δ 8.51 (s, 1H, Ar—H), 8.46 (s, 1H, Ar—H), 8.34 (d, 2H, Ar—H, J=9.3), 7.47 (d, 2H, Ar—H, J=8.8), 6.55 (t, 1H, H-1', J=6.4), 4.65 (m, 1H, H-4', J=3.4), 3.91 (dd, 1H, H-5', J=11.2, 3.4), 3.80 (dd, 1H, H-5', J=11.2, 2.9), 2.65 (app quint, 1H, H-2', J$_{app}$~6.3), 2.50 (ddd, 1H, H-2', J=13.2, 6.1, 4.2), 0.92 (s, 18H, tert-Bu), 0.113, 0.11 (2 s, 12H, SiCH$_3$). $^{13}$C NMR (126 MHz, CDCl$_3$): δ 158.9, 157.4, 153.1, 151.6, 145.2, 142.4, 125.3, 122.3, 122.2, 88.1, 84.8, 71.8, 62.7, 41.6, 26.0, 25.7, 18.4, 18.0, −4.7, −4.8, −5.4, −5.5. FAB HRMS calcd for C$_{28}$H$_{44}$N$_5$O$_6$Si$_2$ (M$^+$+H) 602.2830. found 602.2813.

Example 13

Synthesis of O$^6$-(4-Nitrophenyl)-2',3',5'-tris-O-(tert-butyldimethylsilyl)inosine

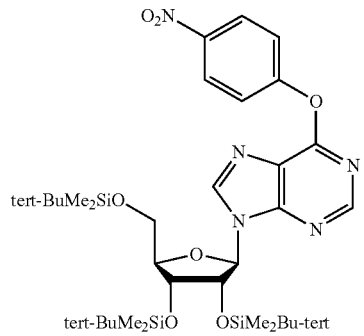

As described for the synthesis of 3',5'-bis-O-(tert-butyldimethylsilyl)-O$^6$-(4-nitrophenyl)-2'-deoxyinosine, this 4-nitrophenyl derivative was prepared by a reaction between O$^6$-(benzotriazol-1-yl)-2',3',5'-tris-O-(tert-butyldimethylsilyl)inosine (27) (71.8 mg, 0.099 mmol) and 4-nitrophenol (27.8 mg, 0.200 mmol) in the presence of Cs$_2$CO$_3$ (65.2 mg, 0.200 mmol) in dry DME (1.0 mL) at 85° C. over 1 h. Chromatographic purification (SiO$_2$, elution with 20% EtOAc in hexanes) afforded 59.5 mg (81% yield) of the title compound as a clear gum. R$_f$(20% EtOAc in hexanes)=0.43. $^1$H NMR (500 MHz, CDCl$_3$): δ 8.53 (s, 1H, Ar—H), 8.51 (s, 1H, Ar—H), 8.35-8.33 (m, 2H, Ar—H), 7.48 (d, 2H, Ar—H, J=9.3), 6.15 (d, 1H, H-1', J=4.9), 4.61 (t, 1H, H-2', J=4.6), 4.34 (t, 1H, H-3', J=4.2), 4.17 (q, 1H, H-4', J=3.3), 4.05 (dd, 1H, H-5', J=11.5, 3.7), 3.82 (dd, 1H, H-5', J=11.5, 2.2), 0.97, 0.94, 0.81 (3 s, 27H, tert-Bu), 0.17, 0.16, 0.11, 0.10, −0.01, −0.18 (6 s, 18H, SiCH$_3$). $^{13}$C NMR (126 MHz, CDCl$_3$): δ 158.8, 157.3, 153.3, 151.7, 145.1, 142.8, 125.4, 122.4, 122.1, 88.6, 85.5, 76.4, 71.7, 62.4, 26.1, 25.8, 25.6, 18.5, 18.1, 17.8, −4.4, −4.7, −4.72, −5.0, −5.3, −5.4. FAB HRMS calcd for C$_{34}$H$_{58}$N$_5$O$_7$Si$_3$ (M$^+$+H) 732.3644. found 732.3629.

Example 14

Synthesis of 3',5'-Bis-O-(tert-butyldimethylsilyl)-O$^6$-(3-cyanophenyl)-2'-deoxyinosine

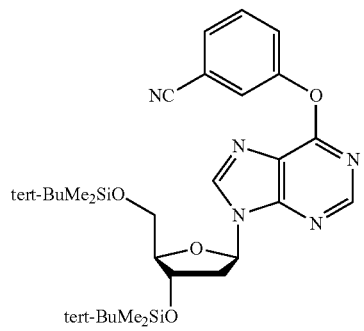

As described for the synthesis of 3',5'-bis-O-(tert-butyldimethylsilyl)-O$^6$-(4-nitrophenyl)-2'-deoxyinosine, this 3-cyanophenyl derivative was prepared by a reaction between O$^6$-(benzotriazol-1-yl)-3',5'-bis-O-(tert-butyldimethylsilyl)-2'-deoxyinosine (26) (59.8 mg, 0.100 mmol) and 3-cyanophenol (13.1 mg, 0.110 mmol) in the presence of Cs$_2$CO$_3$ (65.2 mg, 0.200 mmol) in dry DME (1.0 mL) at 85° C. over 2 h. Chromatographic purification (SiO$_2$, elution with 20% EtOAc in hexanes) afforded 47.5 mg (82% yield) of the title compound as a clear gum. R$_f$(50% EtOAc in hexanes)=0.58. $^1$H NMR (500 MHz, CDCl$_3$): δ 8.49 (s, 1H, Ar—H), 8.45 (s, 1H, Ar—H), 7.62-7.54 (m, 4H, Ar—H), 6.54 (t, 1H, H-1', J=6.4), 4.64 (m, 1H, H-3'), 4.05 (q, 1H, H-4', J=3.4), 3.91 (dd, 1H, H-5', J=11.2, 3.9), 3.80 (dd, 1H, H-5', J=11.2, 3.9), 2.64 (app quint, 1H, H-2', J$_{app}$~6.3), 2.49 (ddd, 1H, H-2', J=13.2, 6.3, 4.4), 0.92, 0.916 (2 s, 18H, tert-Bu), 0.11, 0.105 (2 s, 12H, SiCH$_3$). $^{13}$C NMR (126 MHz, CDCl$_3$): δ 159.1, 153.0, 152.7, 151.6, 142.2, 130.4, 129.2, 126.7, 125.6, 122.1, 117.9, 113.6, 88.1, 84.8, 71.8, 62.7, 41.5, 25.9, 25.7, 18.4, 17.9, −4.7, −4.8, −5.4, −5.5. FAB HRMS calcd for C$_{29}$H$_{44}$N$_5$O$_4$Si$_2$ (M$^+$+H) 582.2932. found 582.2927.

Example 15

Synthesis of 3',5'-Bis-O-(tert-butyldimethylsilyl)-O$^6$-(naphth-1-yl)-2'-deoxyinosine

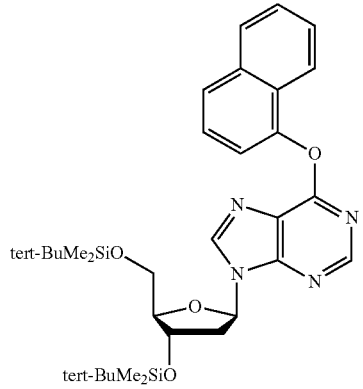

As described for the synthesis of 3',5'-bis-O-(tert-butyldimethylsilyl)-O$^6$-(4-nitrophenyl)-2'-deoxyinosine, this naphthyl derivative was prepared by a reaction between O$^6$-(benzotriazol-1-yl)-3',5'-bis-O-(tert-butyldimethylsilyl)-2'-deoxyinosine (26) (59.8 mg, 0.100 mmol), Cs$_2$CO$_3$ (65.2 mg, 0.200 mmol) and 1-naphthol (15.9 mg, 0.110 mmol) in dry DME (1.0 mL) at 85° C. for 2 h. Chromatographic purification (SiO$_2$, elution with 20% EtOAc in hexanes) afforded 49.2 mg (81% yield) of the title compound as a yellowish-white foam. R$_f$(20% EtOAc in hexanes)=0.37. $^1$H NMR (500 MHz, CDCl$_3$): δ 8.44 (s, 1H, Ar—H), 8.41 (s, 1H, Ar—H), 7.93 (d, 1H, Ar—H, J=8.8), 7.91 (d, 1H, Ar—H, J=8.3), 7.81 (d, 1H, Ar—H, J=8.3), 7.54 (t, 1H, Ar—H, J=7.8), 7.50 (t, 1H, Ar—H, J=7.6), 7.42 (t, 1H, Ar—H, J=7.6), 7.39 (d, 1H, Ar—H, J=7.3), 6.56 (t, 1H, H-1', J=6.4), 4.67 (m, 1H, H-3'), 4.06 (q, 1H, H-4', J=3.4), 3.92 (dd, 1H, H-5', J=11.2, 4.4), 3.82 (dd, 1H, H-5', J=11.2, 2.9), 2.71 (quint, 1H, H-2', J=6.3), 2.50 (ddd, 1H, H-2', J=12.9, 5.9, 4.1), 0.94, 0.93 (2 s, 18H, tert-Bu), 0.12 (s, 12H, SiCH$_3$). $^{13}$C NMR (126 MHz, CDCl$_3$): δ 160.7, 152.7, 152.1, 148.6, 141.7, 134.9, 127.9, 127.3, 126.4, 126.2, 125.9, 125.5, 122.0, 121.9, 118.1, 88.1, 84.7, 71.9, 62.8, 41.4, 25.9, 25.7, 18.4, 18.0, −4.7, −4.8, −5.4, −5.5. FAB HRMS calcd for C$_{32}$H$_{47}$N$_4$O$_4$Si$_2$ (M$^+$+H) 607.3136. found 607.3120.

Example 16

Synthesis of 3',5'-Bis-O-(tert-butyldimethylsilyl)-O$^6$-(fluoren-2-yl)-2'-deoxyinosine

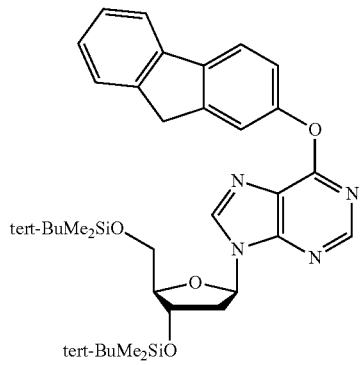

As described for the synthesis of 3',5'-bis-O-(tert-butyldimethylsilyl)-O$^6$-(4-nitrophenyl)-2'-deoxyinosine, this fluorenyl derivative was prepared by a reaction between O$^6$-(benzotriazol-1-yl)-3',5'-bis-O-(tert-butyldimethylsilyl)-2'-deoxyinosine (26) (59.8 mg, 0.100 mmol), Cs$_2$CO$_3$ (65.2 mg, 0.200 mmol) and 2-hydroxyfluorene (20.0 mg, 0.110 mmol) in dry DME (1.0 mL) at 85° C. for 1 h. Chromatographic purification (SiO$_2$, elution with 20% EtOAc in hexanes) afforded 56.0 mg (87% yield) of the title compound as a clear, yellowish gum. R$_f$(20% EtOAc in hexanes)=0.31. $^1$H NMR (500 MHz, CDCl$_1$): δ 8.52 (s, 1H, Ar—H), 8.41 (s, 1H, Ar—H), 7.83 (d, 1H, Ar—H, J=8.3), 7.77 (d, 1H, Ar—H, J=7.3), 7.53 (d, 1H, Ar—H, J=7.3), 7.45 (s, 1H, Ar—H), 7.37 (t, 1H, Ar—H, J=7.6), 7.29 (t, 1H, Ar—H, J=7.8), 6.55 (t, 1H, H-1', J=6.4), 4.66 (m, 1H, H-3'), 4.05 (q, 1H, H-4', J=3.4), 3.94 (s, 2H, CH$_2$), 3.92 (dd, 1H, H-2', J=11.2, 4.1), 3.81 (dd, 1H, H-2', J=11.2, 2.9), 2.67 (app quint, 1H, H-2', J$_{app}$~6.3), 2.50 (ddd, 1H, H-2', J=13.2, 6.0, 4.3), 0.94, 0.93 (2 s, 18H, tert-Bu), 0.12 (s, 12H, SiCH$_3$). $^{13}$C NMR (126 MHz, CDCl$_1$): δ 160.5, 152.5, 152.1, 151.6, 144.7, 143.3, 141.6, 141.1, 139.5, 126.8, 126.5, 124.9, 122.2, 120.5, 120.47, 119.7, 118.7, 88.1, 84.7, 71.9, 62.8, 41.5, 37.0, 25.9, 25.7, 18.4, 18.0, −4.7, −4.8, −5.4, −5.5. FAB HRMS calcd for C$_{35}$H$_{49}$N$_4$O$_4$Si$_2$ (M$^+$+H) 645.3292. found 645.3303.

Example 17

Synthesis of 3',5'-Bis-O-(tert-butyldimethylsilyl)-O$^6$-(quinolin-8-yl)-2'-deoxyinosine

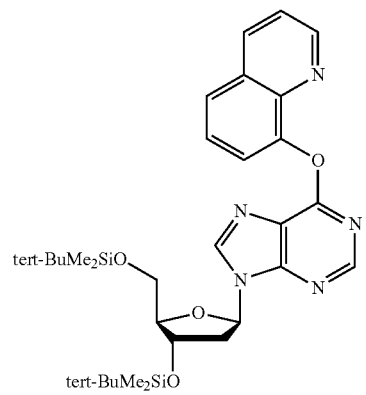

As described for the synthesis of 3',5'-bis-O-(tert-butyldimethylsilyl)-O$^6$-(4-nitrophenyl)-2'-deoxyinosine, this quinolinyl derivative was prepared by a reaction between O⁶-(benzotriazol-1-yl)-3',5'-bis-O-(tert-butyldimethylsilyl)-2'-deoxyinosine (26) (59.8 mg, 0.100 mmol), $Cs_2CO_3$ (65.2 mg, 0.200 mmol) and 8-hydroxyquinoline (16.0 mg, 0.110 mmo) in dry DME (1.0 mL) at 85° C. for 1 h. Chromatographic purification ($SiO_2$, elution with 50% EtOAc in hexanes) afforded 48.0 mg (79% yield) of the title compound as a clear gum. $R_f$(50% EtOAc in hexanes)=0.24. ¹H NMR (500 MHz, $CDCl_1$): δ 8.77 (dd, 1H, Ar—H, J=4.1, 1.2), 8.43 (s, 1H, Ar—H), 8.35 (s, 1H, Ar—H), 8.21 (br d, Ar—H, J=8.3), 7.79 (d, 1H, Ar—H, J=7.8), 7.66-7.60 (m, 2H, Ar—H), 7.40 (dd, 1H, Ar—H, J=8.3, 3.9), 6.54 (t, 1H, H-1', J=6.3), 4.64 (m, 1H, H-3'), 4.04 (q, 1H, H-4', J=3.4), 3.92 (dd, 1H, H-5', J=11.2, 3.9), 3.81 (dd, 1H, H-5', J=11.2, 2.9), 2.66 (app quint, 1H, H-2', $J_{app}$~6.3), 2.48 (ddd, 1H, H-2', J=13.2, 5.9, 4.4), 0.94, 0.92 (2 s, 18H, tert-Bu), 0.123, 0.12, 0.11 (3 s, 12H, $SiCH_3$). ¹³C NMR (126 MHz, $CDCl_3$): δ 161.0, 152.6, 151.9, 150.3, 149.0, 141.6, 141.5, 135.9, 129.7, 126.4, 126.0, 121.9, 121.63, 121.6, 87.9, 84.5, 71.7, 62.7, 41.5, 26.0, 25.8, 18.5, 18.0, −4.6, −4.8, −5.3, −5.4. FAB HRMS calcd for $C_{31}H_{46}N_5O_4Si_2$ (M⁺+H) 608.3088. found 608.3070.

Example 18

Synthesis of O⁶-(Quinolin-8-yl)-2',3',5'-tris-O-(tert-butyldimethylsilyl)inosine

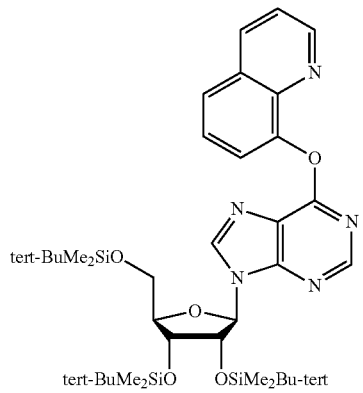

As described for the synthesis of 3',5'-bis-O-(tert-butyldimethylsilyl)-O⁶-(4-nitrophenyl)-2'-deoxyinosine, this quinolinyl derivative was prepared by a reaction between O⁶-(benzotriazol-1-yl)-2',3',5'-tris-O-(tert-butyldimethylsilyl)inosine (27) (71.8 mg, 0.099 mmol), $Cs_2CO_3$ (65.2 mg, 0.200 mmol) and 8-hydroxyquinoline (16.0 mg, 0.110 mmol) in dry DME (1.0 mL) at 85° C. for 1 h. Chromatographic purification ($SiO_2$, elution with 50% EtOAc in hexanes) afforded 52.9 mg (72% yield) of the title compound as a white foam. $R_f$(50% EtOAc in hexanes)=0.58. ¹H NMR (500 MHz, $CDCl_3$): δ 8.74 (m, 1H, Ar—H), 8.48 (s, 1H, Ar—H), 8.33 (s, 1H, Ar—H), 8.20 (m, 1H, Ar—H), 7.79 (d, 1H, Ar—H, J=8.3), 7.67-7.60 (m, 2H, Ar—H), 7.39 (dd, 1H, Ar—H, J=8.5, 4.2), 6.13 (d, 1H, H-1', J=4.4), 4.63 (t, 1H, H-2', J=4.4), 4.37 (t, 1H, H-3', J=4.1), 4.17 (m, 1H, H-4'), 4.07 (dd, 1H, H-5', J=11.2, 3.4), 3.83 (dd, 1H, H-5', J=11.2, 2.4), 0.97, 0.94, 0.84 (3S, 27H, tert-Bu), 0.17, 0.15, 0.12, 0.11, 0.0, −0.11 (6 s, 18H, $SiCH_3$). ¹³C NMR (126 MHz, $CDCl_3$): δ 161.0, 152.9, 151.9, 150.2, 149.1, 141.9, 141.5, 135.9, 129.7, 126.4, 125.9, 122.0, 121.6, 121.5, 88.7, 85.1, 76.2, 71.5, 62.3, 26.1, 25.8, 25.7, 18.6, 18.1, 17.9, −4.3, −4.7, −4.73, −4.9, −5.3, −5.4. FAB HRMS calcd for $C_{37}H_{60}N_5O_5Si_3$ (M⁺+H) 738.3902. found 738.3885.

Example 19

Synthesis of 6-(N-Boc-tyrosine methyl ester) purine-2'-deoxyribonucleoside conjugate

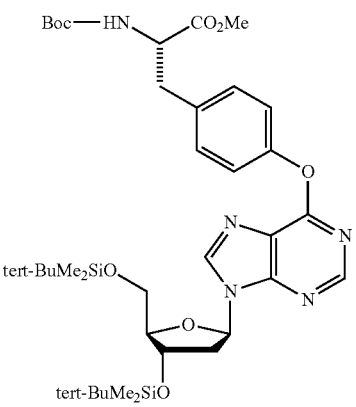

In a clean, dry reaction vial equipped with a stirring bar was placed O⁶-(benzotriazol-1-yl)-2',3'-bis-O-(tert-butyldimethylsilyl)-2'-deoxyinosine (26) (59.8 mg, 0.100 mmol), $NaHCO_3$ (33.6 mg, 0.400 mmol) and Boc-L-tyrosine methyl ester (32.5 mg, 0.110 mmol). Dry DME (1.0 mL) was added and the reaction mixture was allowed to stir at 85° C. for 24 h. The reaction mixture was diluted with EtOAc and washed with water followed by brine. Chromatographic purification ($SiO_2$, elution with 20% acetone in hexanes) afforded 31.0 mg (41% yield) of the title compound as a clear yellowish gum. $R_f$(50% EtOAc in hexanes)=0.53. ¹H NMR (500 MHz, $CDCl_3$): δ 8.49 (s, 1H, Ar—H), 8.40 (s, 1H, Ar—H), 7.21 (s, 4H, Ar—H), 6.53 (t, 1H, H-1', J=6.4), 5.03 (br d, 1H, NH, J=8.3, $CD_3OD$ exchangeable), 4.65-4.60 (m, 2H, H-3' and CH), 4.04 (q, 1H, H-4', J=3.4), 3.90 (dd, 1H, H-5', J=11.2, 3.9), 3.80 (dd, 1H, H-5', J=11.2, 2.9), 3.73 (s, 3H, $OCH_3$), 3.16 (dd, 1H, $PhCH_A$, J=13.9, 5.6), 3.08 (dd, 1H, $PhCH_B$, J=13.9, 6.6), 2.64 (app quint, 1H, H-2', $J_{app}$~6.3), 2.48 (ddd, 1H, H-2', J=13.2, 5.9, 3.9), 1.43 (s, 9H, tert-BuO), 0.93, 0.92 (2 s, 18H, tert-BuSi), 0.11 (s, 12H, $SiCH_3$). ¹³C NMR (126 MHz, $CDCl_3$): δ 172.3, 160.1, 155.1, 152.4, 151.9, 151.4, 141.7, 133.5, 130.4, 122.0, 121.9, 88.0, 84.6, 80.0, 71.74, 71.72, 62.7, 54.3, 52.3, 41.5, 37.8, 28.3, 26.0, 25.7, 18.4, 18.0, −4.7, −4.8, −5.4, −5.5. FAB HRMS calcd for $C_{37}H_{60}N_5O_8Si_2$ (M⁺+H) 758.3980. found 758.4008.

Example 20

Synthesis of 1,4-Bis-[O⁶-(3',5'-bis-O-tert-butyldimethylsilyl)-2'-deoxyinosyl]phenyl ether

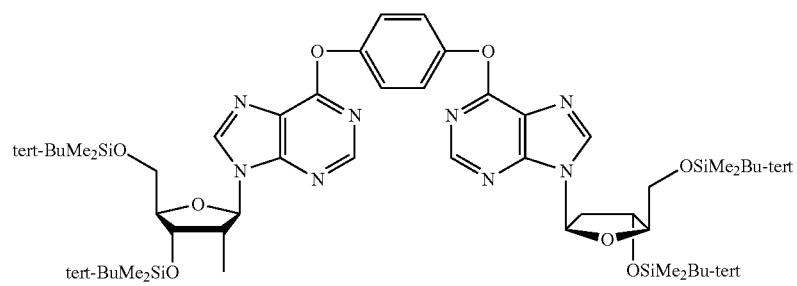

As described for the synthesis of 3',5'-bis-O-(tert-butyldimethylsilyl)-O⁶-(4-nitrophenyl)-2'-deoxyinosine, this dimeric product was prepared by a reaction between O⁶-(benzotriazol-1-yl)-2',3'-bis-O-(tert-butyldimethylsilyl)-2'-deoxyinosine (26) (59.8 mg, 0.100 mmol), $Cs_2CO_3$ (65.2 mg, 0.200 mmol) and hydroquinone (4.4 mg, 0.040 mmol) in dry DME (1.0 mL) at 85° C. for 3 h. Purification by preparative thin layer chromatography ($SiO_2$, elution with 50% EtOAc in hexanes) afforded 35.0 mg (68% yield) of the title compound as a clear, yellowish gum. $R_f$ (3% MeOH in $CH_2Cl_2$)=0.14. ¹H NMR (500 MHz, $CDCl_3$): δ 8.52 (s, 2H, Ar—H), 8.40 (s, 2H, Ar—H), 7.37 (s, 4H, Ar—H), 6.54 (t, 2H, H-1', J=6.3), 4.65 (m, 2H, H-3'), 4.05 (q, 2H, H-4', J=3.4), 3.91 (dd, 2H, H-5', J=11.2, 3.9), 3.80 (dd, 2H, H-5', J=11.2, 2.9), 2.66 (app quint, 2H, H-2', $J_{app}$~6.3), 2.49 (ddd, 2H, H-2', J=13.2, 5.9, 4.4), 0.93, 0.92 (2 s, 36H, tert-Bu), 0.11 (s, 24H, $SiCH_3$). ¹³C NMR (126 MHz, $CDCl_3$): δ 160.0, 152.6, 151.9, 149.7, 141.6, 122.7, 122.2, 88.1, 84.7, 71.9, 62.8, 41.4, 25.9, 25.7, 18.4, 17.9, −4.7, −4.8, −5.4, −5.5. FAB HRMS calcd for $C_{50}H_{84}N_8O_8Si_4$ (M⁺+H) 1035.5411. found 1035.5377.

Example 21

Synthesis of 6-(Morpholin-4-yl)-9-[2-deoxy-3,5-bis-O-(tert-butyldimethylsilyl)-β-D-erythro-pentofuranosyl]purine

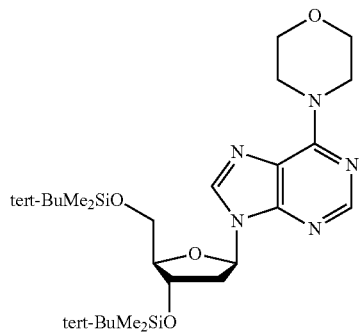

In a clean, dry reaction vial equipped with a stirring bar were placed O⁶-(benzotriazol-1-yl)-3',5'-bis-O-(tert-butyldimethylsilyl)-2'-deoxyinosine (26) (59.8 mg, 0.100 mmol), $Cs_2CO_3$ (65.2 mg, 0.200 mmol) and dry DME (1.0 mL). Morpholine (17.5 μL, 0.200 mmol) was added, the reaction mixture was flushed with $N_2$, and the mixture was allowed to stir at room temperature for 1 h. The reaction mixture was concentrated and the residue was dissolved in EtOAc. The mixture was washed with 10% aq citric acid, sat aq $NaHCO_3$ and brine. The organic layer was dried over $Na_2SO_4$ and evaporated to dryness. No additional purification was needed and 43 mg (78% yield) of the title compound was obtained. $R_f$ (3% MeOH in $CH_2Cl_2$)=0.18. ¹H NMR (500 MHz, $CDCl_3$): δ 8.34 (s, 1H, Ar—H), 8.02 (s, 1H, Ar—H), 6.46 (t, 1H, H-1', J=6.6), 4.59 (m, 1H, H-3'), 4.30 (br s, 4H, $2CH_2$), 4.01 (app q, 1H, H-4', $J_{app}$~3.4), 3.85-3.82 (m, 5H, H-5' and $2CH_2$), 3.76 (dd, 1H, H-5', J=11.0, 3.2), 2.59 (app quint, 1H, H-2', $J_{app}$~6.5), 2.42 (ddd, 1H, H-2', J=13.2, 5.9, 3.9), 0.91 (s, 18H, tert-Bu), 0.09, 0.08, 0.076 (3 s, 12H, $SiCH_3$). ¹³C NMR (126 MHz, $CDCl_3$): δ 153.9, 152.3, 150.6, 136.8, 120.4, 87.8, 84.1, 72.0, 67.0, 62.8, 45.6, 41.1, 26.0, 25.7, 18.4, 18.0, −4.7, −4.8, −5.4, −5.5. FAB HRMS calcd for $C_{26}H_{48}N_5O_4Si_2$ (M⁺+H) 550.3245. found 550.3222.

Example 22

Synthesis of 6-(Morpholin-4-yl)-9-[2,3,5-tris-O-(tert-butyldimethylsilyl)-β-D-ribofuranosyl]purine

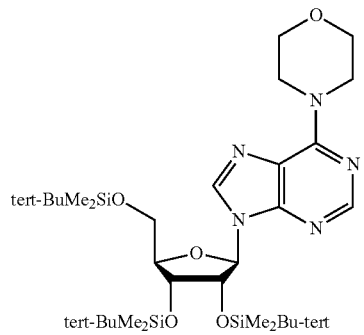

As described for the synthesis of 6-(morpholin-1-yl)-9-[2-deoxy-3,5-bis-O-(tert-butyldimethylsilyl)-β-D-erythro-pentofuranosyl]-purine, this morpholino derivative was prepared by a reaction between O⁶-(benzotriazol-1-yl)-2',3',5'-tris-O-(tert-butyldimethylsilyl)-inosine (27) (71.8 mg, 0.099 mmol), and morpholine (17.5 μL, 0.200 mmol) in the presence of $Cs_2CO_3$ (65.2 mg, 0.200 mmol) in dry DME (1.0 mL) at room temperature over 1 h. No additional purification was needed and 57.5 mg (85% yield) of the title compound was obtained. $R_f$ (3% MeOH in $CH_2Cl_2$)=0.68. ¹H NMR (500 MHz, $CDCl_3$): δ 8.33 (s, 1H, Ar—H), 8.03 (s, 1H, Ar—H), 6.03 (d, 1H, H-1', J=5.4), 4.72 (t, 1H, H-2', J=4.9), 4.32-4.29 (br m, 5H, H-3' and $2CH_2$), 4.11 (q, 1H, H-4', J=3.6), 4.02 (dd, 1H, H-5', J=11.2, 4.4), 3.83 (t, 4H, $2CH_2$, J=4.6), 3.77 (dd, 1H, H-5', J=11.2, 3.2), 0.95, 0.93, 0.80 (3 s, 27H, tert-Bu), 0.124, 0.12, 0.104, 0.10, −0.05, −0.22 (6 s, 18H, $SiCH_3$). ¹³C NMR (126 MHz, $CDCl_3$): δ 153.9, 152.2, 150.9, 137.7, 120.5, 88.1, 85.4, 75.4, 72.1, 67.0, 62.6, 45.6, 26.1, 25.8, 25.7, 18.5, 18.1, 17.9, −4.4, −4.7, −5.0, −5.4, −5.41.

Example 23

Synthesis of 9-(2-Deoxy-β-D-erythro-pentofuranosyl)-6-(morpholin-4-yl)purine

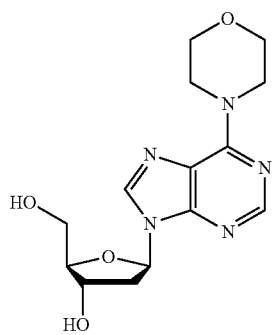

As described for the synthesis of 6-(morpholin-1-yl)-9-[2-deoxy-3,5-bis-O-(tert-butyldimethylsilyl)-β-D-erythropentofuranosyl]purine, this morpholino derivative was prepared by a reaction between O⁶-(benzotriazol-1-yl)-2'-deoxyinosine (28) (36.9 mg, 0.100 mmol), and morpholine (17.5 μL, 0.200 mmol) in the presence of $Cs_2CO_3$ (65.2 mg, 0.200 mmol) in dry DME (1.0 mL) at room temperature over 1 h. Chromatographic purification ($SiO_2$, elution with 5% MeOH in $CH_2Cl_2$) afforded 16.6 mg (52% yield) of the title compound as a clear gum. $R_f$(10% MeOH in $CH_2Cl_2$)=0.34. ¹H NMR (500 MHz, $CDCl_3$): δ 8.26 (s, 1H, Ar—H), 7.77 (s, 1H, Ar—H), 6.88 (br, 1H, OH, $CD_3OD$ exchangeable), 6.30 (dd, 1H, H-1', J=9.8, 5.4), 4.77 (d, 1H, H-3', J=4.8), 4.30 (br, 4H, $2CH_2$), 4.21 (br s, 1H, H-4'), 3.96 (dd, 1H, H-5', J=12.7, 1.2), 3.81 (t, 4H, $2CH_2$, J=4.9), 3.77 (br d, 1H, H-5', J=13.2), 3.10 (ddd, 1H, H-2', J=13.7, 9.3, 4.9), 2.65 (br, 1H, OH, $CD_3OD$ exchangeable), 2.26 (dd, 1H, H-2', J=13.7, 5.6). ¹³C NMR (126 MHz, $CDCl_3$): δ 154.1, 151.6, 149.4, 138.3, 121.7, 89.7, 87.8, 73.6, 67.0, 63.5, 45.6, 40.5.

Example 24

Synthesis of 6-(Morpholin-4-yl)-9-(β-D-ribofuranosyl)purine

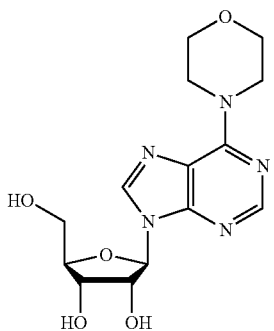

As described for the synthesis of 3',5'-bis-O-(tert-butyldimethylsilyl)-O⁶-methyl-2'-deoxyinosine, this morpholino derivative was prepared by a reaction between O⁶-(benzotriazol-1-yl)inosine (29) (38.5 mg, 0.100 mmol), $Cs_2CO_3$ (65.2 mg, 0.200 mmol) and morpholine (17.5 μL, 0.200 mmol) in dry DME (1.0 mL). Chromatographic purification ($SiO_2$, elution with 10% MeOH in $CH_2Cl_2$) gave a slightly impure material (~77% yield). Recrystallization from MeOH afforded 19.6 mg (58% yield) of the title compound as a white solid. $R_f$(10% MeOH in $CH_2Cl_2$)=0.27. ¹H NMR (500 MHz, DMSO-$d_6$): δ 8.47 (s, 1H, Ar—H), 8.30 (s, 1H, Ar—H), 5.96 (d, 1H, H-1', J=5.9), 5.51 (d, 1H, OH, J=6.4, $D_2O$ exchangeable), 5.35 (dd, 1H, OH-5', J=6.8, 4.9, $D_2O$ exchangeable), 5.24 (d, 1H, OH, H=4.9, $D_2O$ exchangeable), 4.61 (q, 1H, H-2', J=5.6), 4.25 (br, 4H, $2CH_2$), 4.18 (app q, 1H, H-3', $J_{app}$~4.4), 4.00 (q, 1H, H-4', J=3.4), 3.75 (t, 4H, $2CH_2$, J=4.9), 3.71 (dt, 1H, H-5', J=11.7, 4.4), 3.59 (ddd, 1H, H-5', J=11.7, 6.8, 3.9). ¹³C NMR (126 MHz, DMSO-$d_6$): δ 154.0, 152.5, 151.0, 139.7, 120.4, 88.5, 86.4, 74.2, 71.2, 66.9, 62.2, 46.0.

Example 25

Synthesis of 6-(Imidazol-1-yl)-9-[2-deoxy-3,5-bis-O-(tert-butyldimethylsilyl)-β-D-erythro-pentofuranosyl]purine

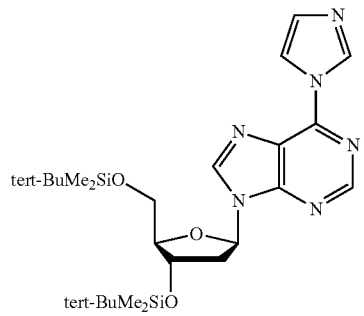

In a clean, dry reaction vial equipped with a stirring bar were placed O⁶-(benzotriazol-1-yl)-2',3'-bis-O-(tert-butyldimethylsilyl)-2'-deoxyinosine (26) (59.8 mg, 0.100 mmol), $Cs_2CO_3$ (65.2 mg, 0.200 mmol) and imidazole (13.6 mg, 0.200 mmol). Dry DME (1.0 mL) was added and the reaction mixture was flushed with $N_2$ and the mixture was allowed to stir at 85° C. for 4 h. The reaction mixture was concentrated and the residue was dissolved in EtOAc. The mixture was washed with water, dried over $Na_2SO_4$, and evaporated to dryness. Chromatographic purification ($SiO_2$, elution with 50% EtOAc in hexanes) afforded 32.0 mg (60% yield) of the title compound as a clear gum. $R_f$(20% EtOAc in hexanes)=0.07. ¹H NMR (500 MHz, $CDCl_3$): δ 9.19 (s, 1H, Ar—H), 8.77 (s, 1H, Ar—H), 8.48 (s, 1H, Ar—H), 8.40 (s, 1H, Ar—H), 7.25 (s, 1H, Ar—H), 6.56 (t, 1H, H-1', J=6.3), 4.64 (app q, 1H, H-3', $J_{app}$~4.2), 4.06 (m, 1H, H-4'), 3.90 (dd, 1H, J=11.2, 3.9), 3.80 (dd, 1H, H-5', J=11.2, 2.9), 2.65 (app quint, 1H, H-2', $J_{app}$~6.3), 2.51 (m, 1H, H-2'), 0.92, 0.915 (2 s, 18H, tert-Bu), 0.11, 0.10 (2 s, 12H, $SiCH_3$). ¹³C NMR (126 MHz, $CDCl_3$): δ 153.0, 152.1, 145.6, 143.0, 137.7, 130.6, 122.9, 117.3, 88.1, 84.7, 71.7, 62.6, 41.5, 25.9, 25.7, 18.4, 18.0, −4.7, −4.8, −5.4, −5.5.

Example 26

Synthesis of 3',5'-Bis-O-(tert-butyldimethylsilyl)-N⁶-benzyl-2'-deoxyadenosine

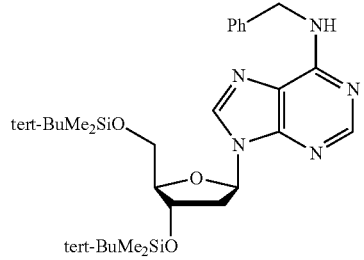

As described for the synthesis of 6-(morpholin-1-yl)-9-[2-deoxy-3,5-bis-O-(tert-butyldimethylsilyl)-β-D-erythro-pentofuranosyl]purine, the benzyl derivative was prepared by a reaction between O⁶-(benzotriazol-1-yl)-3',5'-bis-O-(tert-butyldimethylsilyl)-2'-deoxyinosine (26) (59.8 mg, 0.100 mmol) and benzylamine (21.8 μL, 0.200 mmol) in the presence of Cs$_2$CO$_3$ (65.2 mg, 0.200 mmol) in dry DME (1.0 mL) at room temperature over 6 h. Chromatographic purification (SiO$_2$, elution with 20% EtOAc in hexanes followed by 50% EtOAc in hexanes) afforded 35.0 mg (84% yield) of the title compound as a clear gum. R$_f$ (3% MeOH in CH$_2$Cl$_2$)=0.07. $^1$H NMR (500 MHz, CDCl$_3$): δ 8.41 (s, 1H, Ar—H), 8.11 (s, 1H, Ar—H), 7.38 (d, 2H, Ar—H, J=7.5), 7.33 (t, 2H, Ar—H, J=7.6), 7.28 (m, 1H, Ar—H), 6.45 (t, 1H, H-1', J=6.6), 5.98 (br s, 1H, NH), 4.87 (br s, 2H, CH$_2$), 4.61 (m, 1, H-3'), 4.01 (q, 1H, H-4', J=3.4), 3.87 (dd, 1H, H-5', J=5.9, 4.4), 3.77 (dd, 1H, H-5', J=5.9, 4.4), 2.64 (quint, 1H, H-2'. J=6.3), 2.43 (ddd, 1H, H-2', J=13.2, 6.4, 3.9), 0.91 (s, 18H, tert-Bu), 0.10, 0.09, 0.08 (3 s, 12H, SiCH$_3$). $^{13}$C NMR (126 MHz, CDCl$_3$): δ 154.6, 153.1, 138.4, 128.6, 127.8, 127.5, 120.2, 87.8, 84.3, 71.2, 62.8, 41.2, 25.9, 25.8, 18.4, 18.0, −4.7, −4.8, −5.4, −5.5. FAB HRMS calcd for C$_{29}$H$_{48}$N$_5$O$_3$Si$_2$ (M$^+$+H) 570.3296. found 570.3279.

Example 27

Synthesis of 2',3',5'Tris-O-(tert-butyldimethylsilyl)-N$^6$-benzyladenosine

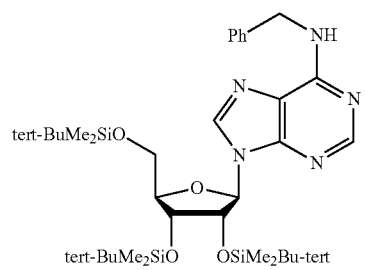

As described for the synthesis of 6-(morpholin-4-yl)-9-[2-deoxy-3,5-bis-O-(tert-butyldimethylsilyl)-β-D-erythro-pentofuranosyl]purine, this benzyl derivative was prepared by a reaction between O$^6$-(benzotriazol-1-yl)-2',3',5'-tris-O-(tert-butyldimethylsilyl)inosine (27) (71.8 mg, 0.099 mmol) and benzylamine (21.8 μL, 0.200 mmol) in the presence of Cs$_2$CO$_3$ (65.2 mg, 0.200 mmol) in dry DME (1.0 mL) at room temperature over 7 h. Chromatographic purification (SiO$_2$, elution with 3% EtOAc in hexanes followed by 20% EtOAc in hexanes) afforded 61.0 mg (87% yield) of the title compound as a clear gum. R$_f$ (20% EtOAc in hexanes)=0.39. $^1$H NMR (500 MHz, CDCl$_3$): δ 8.40 (s, 1H, Ar—H), 8.09 (s, 1H, Ar—H), 7.38 (d, 2H, Ar—H, J=7.3), 7.34 (t, 2H, Ar—H, J~7.3), 7.28 (app t, 1H, Ar—H, J$_{app}$~8.5), 6.02 (d, 1H, H-1', J=5.4), 5.95 (br s, 1H, NH), 4.86 (br s, 2H, CH$_2$), 4.70 (t, 1H, H-2', J=4.9), 4.32 (t, 1H, H-3', J=3.9), 4.12 (q, 1H, H-4', J=3.4), 4.03 (dd, 1H, H-5', J=11.2, 4.1), 3.78 (dd, 1H, H-5', J=11.2, 2.9), 0.95, 0.93, 0.80 (3 s, 27H, tert-Bu), 0.13, 0.12, 0.11, 0.10, −0.04, −0.22 (6 s, 18H, SiCH$_3$). $^{13}$C NMR (126 MHz, CDCl$_3$): δ 154.7, 153.0, 149.4, 139.1, 138.6, 128.6, 127.7, 127.4, 120.4, 88.4, 85.4, 75.6, 72.1, 62.6, 44.8, 26.0, 25.8, 25.7, 18.4, 18.0, 17.8, −4.4, −4.7, −5.1, −5.4.

Example 28

Synthesis of 6-Thiobenzyl-9-[2-deoxy-3,5-bis-O-(tert-butyldimethylsilyl)-β-D-etythro-pentofuranosyl]purine

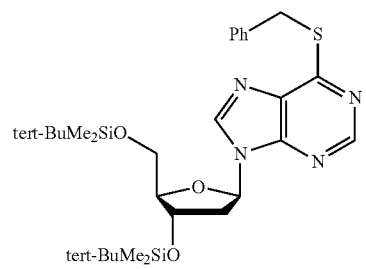

As described for the synthesis of 3',5'-bis-O-(tert-butyldimethylsilyl)-O$^6$-(4-nitrophenyl)-2'-deoxyinosine, this thiobenzyl derivative was prepared by a reaction between O$^6$-(benzotriazol-1-yl)-3',5'-bis-O-(tert-butyldimethylsilyl)-2'-deoxyinosine (26) (59.8 mg, 0.100 mmol) and benzylmercaptan (23.5 μL, 0.200 mmol) in the presence of Cs$_2$CO$_3$ (65.2 mg, 0.200 mmol) in dry DME (1.0 mL) at room temperature over 1 h. Chromatographic purification (SiO$_2$, elution with CH$_2$Cl$_2$ followed by 20% EtOAc in hexanes) afforded 50.1 mg (85% yield) of the title compound as a clear, yellowish gum. R$_f$ (20% EtOAc in hexanes)=0.40. $^1$H NMR (500 MHz, CDCl$_3$): δ 8.73 (s, 1H, Ar—H), 8.27 (s, 1H, Ar—H), 7.47 (d, 2H, Ar—H, J=7.6), 7.31-7.22 (m, 3H, Ar—H), 6.49 (t, 1H, H-1', J=6.4), 4.67 (AB$_{quartet}$, 2H, CH$_2$, J=13.6), 4.62 (m, 1H, H-3'), 4.03 (app q, 1H, H-4', J~3.5), 3.87 (dd, 1H, H-5', J=11.3, 4.3), 3.77 (dd, 1H, H-5', J=11.3, 3.2), 2.65 (m, 1H, H-2'), 2.44 (ddd, 1H, H-2', J=13.1, 6.1, 3.7), 0.92, 0.91, 0.90 (3 s, 18H, tert-Bu), 0.11, 0.08, 0.079 (3 s, 12H, SiCH$_3$). $^{13}$C NMR (126 MHz, CDCl$_3$): δ 160.6, 151.7, 148.1, 141.2, 137.5, 131.7, 129.1, 128.5, 127.2, 88.0, 84.5, 72.0, 62.8, 41.3, 32.8, 26.0, 25.8, 18.4, 18.0, −4.7, −4.8, −5.4, −5.5. FAB HRMS calcd for C$_{29}$H$_{47}$N$_4$O$_3$SSi$_2$ (M$^+$+H) 587.2907. found 587.2906.

Example 29

Synthesis of 6-Thiobenzyl-9-[2,3,5-tris-O-(tert-butyldimethylsilyl)-β-D-erythro-pentofuranosyl]purine

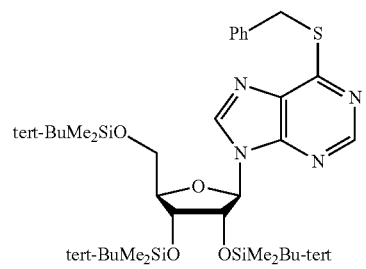

In a clean, dry reaction vial equipped with a stirring bar was placed O$^6$-(benzotriazol-1-yl)-2',3',5'-tris-O-(tert-butyldimethylsilyl)inosine (27) (72.8 mg, 0.100 mmol), Cs$_2$CO$_3$ (65.2 mg, 0.200 mmol) and benzylmercaptan (23.5 μL, 0.200 mmol). Dry DME (1.0 mL) was added and the reaction mixture was allowed to stir at room temperature for 7 h and then concentrated. Chromatographic purification (SiO$_2$, elution with 5% EtOAc in hexanes followed by 20% EtOAc in hexanes) afforded 66.5 mg (93% yield) of the title compound as a clear gum. R$_f$ (20% EtOAc in hexanes)=0.59. $^1$H NMR (500 MHz, CDCl$_3$): δ 8.73 (s, 1H, Ar—H), 8.31 (s, 1H, Ar—H), 7.48-7.46 (m, 2H, Ar—H), 7.32-7.23 (m, 3H, Ar—H), 6.08 (d, 1H, H-1', J=5.2), 4.67 (AB$_{quartet}$, 2H, CH$_2$, J=13.4), 4.66 (app t, 1H), H-2', J$_{app}$~4.8), 4.33 (t, 1H, H-3', J=4.0), 4.14 (q, 1H, H-4', J=3.5), 4.02 (dd, 1H, H-5', J=11.3, 4.0), 3.79 (dd, 1H, H-5', J=11.3, 2.9), 0.95, 0.945, 0.94, 0.80 (4 s, 27H, tert, Bu), 0.14, 0.13, 0.11, 0.105, −0.03, −0.23 (6 s, 18H, SiCH$_3$). $^{13}$C NMR (126 MHz, CDCl$_3$): δ 160.6, 151.8, 148.4, 141.7, 137.5, 131.7, 129.1, 128.5, 127.2, 88.4, 85.5, 75.9, 71.9, 62.5, 32.9, 26.1, 25.8, 25.7, 18.5, 18.1, 17.8, −4.4, −4.7, −4.71, −5.0, −5.4. FAB HRMS calcd for C$_{35}$H$_{61}$N$_4$O$_4$SSi$_3$ (M$^+$+H) 717.3721. found 717.3734.

Example 30

Synthesis of N$^1$-[6-[9-(2-deoxy-3,5-bis-O-(tert-butyldimethylsilyl)-β-D-erythro-pentofuranosyl)]purinyl]-3',5'-bis-O-(tert-butyldimethylsilyl)-2'-deoxyinosine

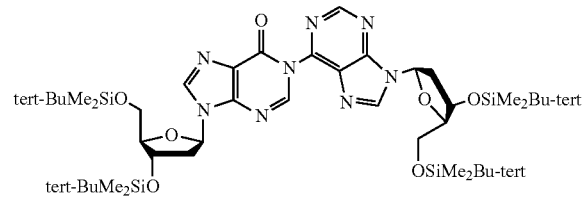

As described for the synthesis of 3',5'-bis-O-(tert-butyldimethylsilyl)-O$^6$-phenyl-2'-deoxyinosine, this unsymmetrical dimer was prepared by a reaction between O$^6$-(benzotriazol-1-yl)-3',5'-bis-O-(tert-butyldimethylsilyl)-2'-deoxyinosine (26) (20.0 mg, 0.0334 mmol) and 3',5'-bis-O-(tert-butyldimethylsilyl)-2'-deoxyinosine (22) (16.1 mg, 0.0334) in the presence of K$_3$PO$_4$ (10.6 mg, 0.050 mmol) in dry toluene (0.33 mL) at 105° C. over 3 h. Chromatographic purification (SiO$_2$, elution with 20% EtOAc in hexanes followed by 5% MeOH in CH$_2$Cl$_2$) afforded 28.9 mg, 92% yield of the title compound as a clear, yellowish gum. R$_f$ (3% MeOH in CH$_2$Cl$_2$)=0.09. $^1$H NMR (500 MHz, CDCl$_3$): δ 8.99 (s, 1H, Ar—H), 8.50 (s, 1H, Ar—H), 8.25 (s, 1H, Ar—H), 8.15 (s, 1H, Ar—H), 6.57 (t, 1H, H-1', J=6.4), 6.43 (app t, 1H, H-1', J$_{app}$~6.3), 4.65-4.60 (m, 2H, 2H-3'), 4.06 (q, 1H, H-4', J=3.4), 4.03 (q, 1H, H-4', J=3.4), 3.88 (dd, 1H, H-5', J=11.2, 3.9), 3.86 (dd, 1H, H-5', J=10.5, 4.2), 3.79 (dd, 2H, 2H-5', J=11.2, 2.9), 2.68 (app quint, 1H, H-2', J$_{app}$~6.3), 2.57 (app quint, 1H, H-2', J$_{app}$~6.3), 2.50 (ddd, 1H, H-2', J=13.2, 6.3, 3.9), 2.45 (ddd, 1H, H-2', J=13.2, 5.9, 3.9), 0.93, 0.92, 0.918, 0.90 (4 s, 36H, tert-Bu), 0.13, 0.12, 0.11, 0.10, 0.09, 0.08, (6 s, 24H, SiCH$_3$). $^{13}$C NMR (126 MHz, CDCl$_3$): δ 155.1, 153.3, 152.2, 147.8, 146.9, 145.9, 144.6, 138.4, 129.9, 124.9, 88.2, 88.1, 84.9, 84.6, 71.9, 71.8, 62.7, 41.8, 41.4, 26.0, 25.7, 18.4, 18.0, −4.7, −4.8, −5.4, −5.5. FAB HRMS calcd for C$_{44}$H$_{79}$N$_8$O$_7$Si$_4$ (M$^+$+H) 943.5149. found 943.5159.

Example 31

Synthesis of O$^6$-(Benzotriazol-1-yl)-5'-O-(4,4'-dimethoxytrityl)-2'-deoxyinosine

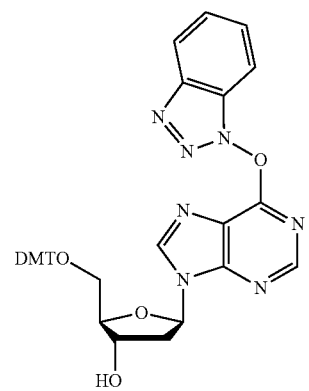

In a 100 mL round-bottomed flask equipped with a stirring bar were placed 5'-O-(4,4'-dimethoxytrityl)-2'-deoxyinosine$^{26}$ (0.7 g, 1.262 mmol), BOP (1.117 g, 2.524 mmol), DIPEA (0.44 mL, 2.524 mmol) and dry THF (50.0 mL). The reaction mixture was allowed to stir at room temperature under a N$_2$ balloon for 40 h. The reaction mixture was evaporated, diluted with EtOAc (200 mL) and washed with brine. The organic layer was dried over Na$_2$SO$_4$ and concentrated. Chromatographic purification (SiO$_2$, packed with 1% DIPEA in EtOAc and elution with EtOAc) afforded 0.718 g (85% yield) of the title compound as a white foam. R$_f$ (EtOAc)= 0.31. $^1$H NMR (500 MHz, CDCl$_3$): δ 8.31 (s, 1H, Ar—H), 8.28 (s, 1H, Ar—H), 8.13 (d, 1H, Ar—H, J=8.2), 7.55-7.45 (m, 3H, Ar—H), 7.38 (d, 2H, Ar—H, J=7.3), 7.29-7.19 (m, 7H, Ar—H), 6.80 (d, 4H, Ar—H, J=8.9), 6.52 (t, 1H, H-1', J=6.4), 4.73 (br m, 1H, H-3'), 4.20 (q, 1H, H-4', J=4.2), 3.77 (s, 6H, OCH$_3$), 3.45 (dd of AB$_{quartet}$, 1H, H-5', J=10.4, 4.6), 3.40 (dd of AB$_{quartet}$, 1H, H-5', J=10.4, 5.0), 2.87 (app quint, 1H, H-2', J$_{app}$~6.6), 2.62 (ddd, 1H, H-2', J=13.4, 6.2, 4.3), 2.39 (d, 1H, 3'-OH, J=3.1). $^{13}$C NMR (126 MHz, CDCl$_3$): δ 159.1, 158.6, 153.5, 151.4, 144.4, 143.5, 135.5, 135.4, 130.0, 128.9, 128.8, 128.0, 127.9, 127.1, 124.8, 120.6, 120.1, 113.2, 108.7, 86.8, 86.3, 85.0, 72.6, 63.5, 55.2, 40.3. FAB HRMS calcd for C$_{37}$H$_{34}$N$_7$O$_6$ (M$^+$+H) 672.2571. found 672.2583.

Example 32

Synthesis of $O^6$-(Benzotriazol-1-yl)-3'-O—[(N,N-diisopropylamino)(β-cyanoethoxy)phosphinyl]-5'-O-(4,4'-dimethoxytrityl)-2'-deoxyinosine

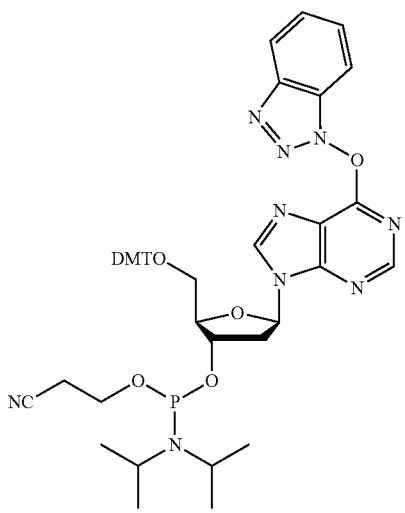

In a clean, dry vial equipped with a stirring bar was placed $O^6$-(benzotriazol-1-yl)-5'-O-(4,4'-dimethoxytrityl)-2'-deoxyinosine (0.030 g, 0.0447 mmol) and the vial was transferred to a glove bag maintained under $N_2$. $CH_2Cl_2$ (0.5 mL), DIPEA (19.5 µL, 0.112 mmol) and 2-cyanoethyl diisopropylchlorophosphoramidite (19.9 µL, 0.0894 mmol) were added. The mixture was removed from the glove bag and allowed to stir at room temperature for 1 h under a $N_2$ atmosphere. The reaction mixture was diluted with $CH_2Cl_2$ and washed with saturated $NaHCO_3$ followed by brine. The organic layer was dried over $Na_2SO_4$ and concentrated. Chromatographic purification ($SiO_2$ packed with 50/50/1 EtOAc/hexanes/DIPEA and eluted with 50% EtOAc in hexanes) afforded 18.4 mg (47% yield) of the title compound as a white, foamy solid. $R_f$ (50/50/1 EtOAc/hexanes/DIPEA)=0.51 and 0.45 for the two phosphoramidite diastereomers. $^{31}$P NMR (202 MHz, $CDCl_3$): δ 150.08 and 150.00.

Example 33

Synthesis of $O^4$-(Benzotriazol-1-yl)-3',5'-bis-O-(tert-butyldimethylsilyl)thymidine

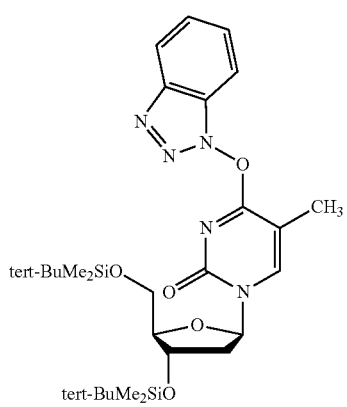

As described for the synthesis of 26, this compound was prepared by a reaction between 3',5'-bis-O-(tert-butyldimethylsilyl)thymidine (0.235 g, 0.998 mmol), BOP (0.443 g, 0.998 mmol) and NaH (47.9 mg, 1.997 mmol) in dry THF (5 mL). Chromatographic purification ($SiO_2$, elution with 3% MeOH in $CH_2Cl_2$) yielded 197 mg (67% yield along with 29% of starting material) of the title compound as a clear gum. $R_f$ (3% MeOH in $CH_2Cl_2$)=0.44. $^1$H NMR (500 MHz, $CDCl_3$): δ 8.16 (s, 1H, vinyl H), 7.54-7.40 (m, 4H, Ar—H), 6.19 (t, H-1', J=6.1), 4.39-4.36 (m, 1H, H-3'), 4.01-3.99 (br m, 1H, H-4'), 3.96 (dd, 1H, H-5', J=11.7, 2.4), 3.80 (dd, 1H, H-5', J=11.7, 2.4), 2.51 (ddd, 1H, 1H, H-2', J=13.2, 6.2, 3.9), 4.04 (app q, 1H, H-2', $J_{app}$=~6.4), 0.96, 0.88 (2 s, 18H, tert-Bu), 0.16, 0.14, 0.07 (3 s, 12H, $SiCH_3$).

Example 34

Synthesis of polystyrene-supported $O^6$-(benzotriazol-1-yl)-3',5'-bis-O-(tert-butyldimethylsilyl)-2'-deoxyinosine (30)

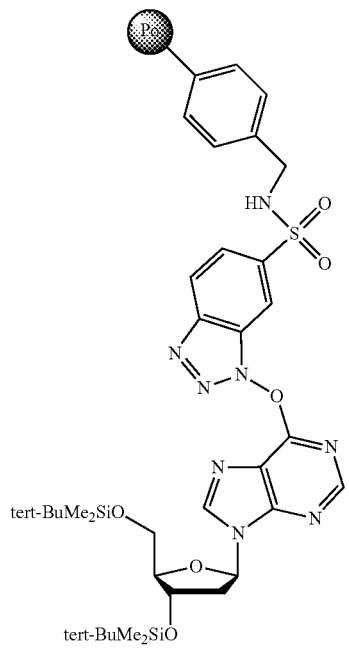

Into a 50 mL round-bottomed flask equipped with a stirring bar were placed $I_2$ (0.914 g, 3.60 mmol) and dry $CH_2Cl_2$ (30 mL). HMPT (0.65 mL, 3.60 mmol) was added slowly and the mixture was stirred at room temperature for 10 min. DIPEA (1.67 mL, 9.60 mmol) and 3',5'-bis-O-(tert-butyldimethylsilyl)-2'-deoxyinosine (22) (1.154 g, 2.40 mmol) were added and the mixture was allowed to stir at room temperature for 1.5 h. PS-HOBt (3.672 g, 3.60 mmol) was added to this solution and the resin suspension was allowed to stir at room temperature for 21 h. The resin was filtered, washed sequentially with $CH_2Cl_2$, 5% MeOH in $CH_2Cl_2$, $CH_2Cl_2$ and $Et_2O$ and then dried under vacuum. The polystyrene-supported $O^6$-(benzotriazol-1-yl)-3',5'-bis-O-(tert-butyldimethylsilyl)-2'-deoxyinosine (30) was obtained as pale brownish resin (4.650 g).

Example 35

Synthesis of polystyrene-supported O⁶-(benzotriazol-1-yl)-2',3',5'-tris-O-(tert-butyldimethylsilyl)inosine (31)

As described for the synthesis of 30, 31 was prepared by a reaction between $I_2$ (0.571 g, 2.25 mmol), HMPT (0.41 mL, 2.25 mmol), DIPEA (1.05 mL, 6.00 mmol) and 2',3',5'-tris-O-(tert-butyldimethylsilyl)inosine (23) (0.917 g, 1.50 mmol) and PS-HOBt (2.206 g, 2.25 mmol) in dry $CH_2Cl_2$ (20 mL). The polystyrene-supported O⁶-(benzotriazol-1-yl)-2',3',5'-tris-O-(tert-butyldimethylsilyl)inosine (31) was obtained as yellow resin (2.793 g).

Example 36

Synthesis of a DNA Building Block and Site-Specific DNA Modification

As shown in the reaction scheme above, reaction of the known 5'-O-DMT-2'-deoxyinosine 32 with 2 mol equivalents each of BOP and (iso-Pr)₂NEt at room temperature over 40 hours led to the O⁶-(benzotriazol-1-yl)-5'-O-DMT-2'-deoxyinosine 33 in 85% isolated yield. Finally, conversion of 33 to the phosphoramidite 34 was accomplished by conventional methods (47% yield).

Compound 34 was incorporated into the 11-mer oligonucleotide 35 using standard phosphoramidite chemistry. The support-bound reactive DNA 35 was then exposed to a DMF solution of morpholine for 24 hours at room temperature. The DNA was subjected to standard cleavage from the support and deprotection followed by LC/MS analysis. This analysis showed the presence of the desired morpholine modified DNA oligomer 36 (mass 3665.7) (SEQ ID NO: 1 and the $T_{10}$ oligomer (mass 2980.3) in a nearly 1:1 ratio indicating the coupling efficiency of 35 to be ~50%. DNA assembly was performed with only 6 mg of compound 35. Coupling efficiency can be substantially improved by altering

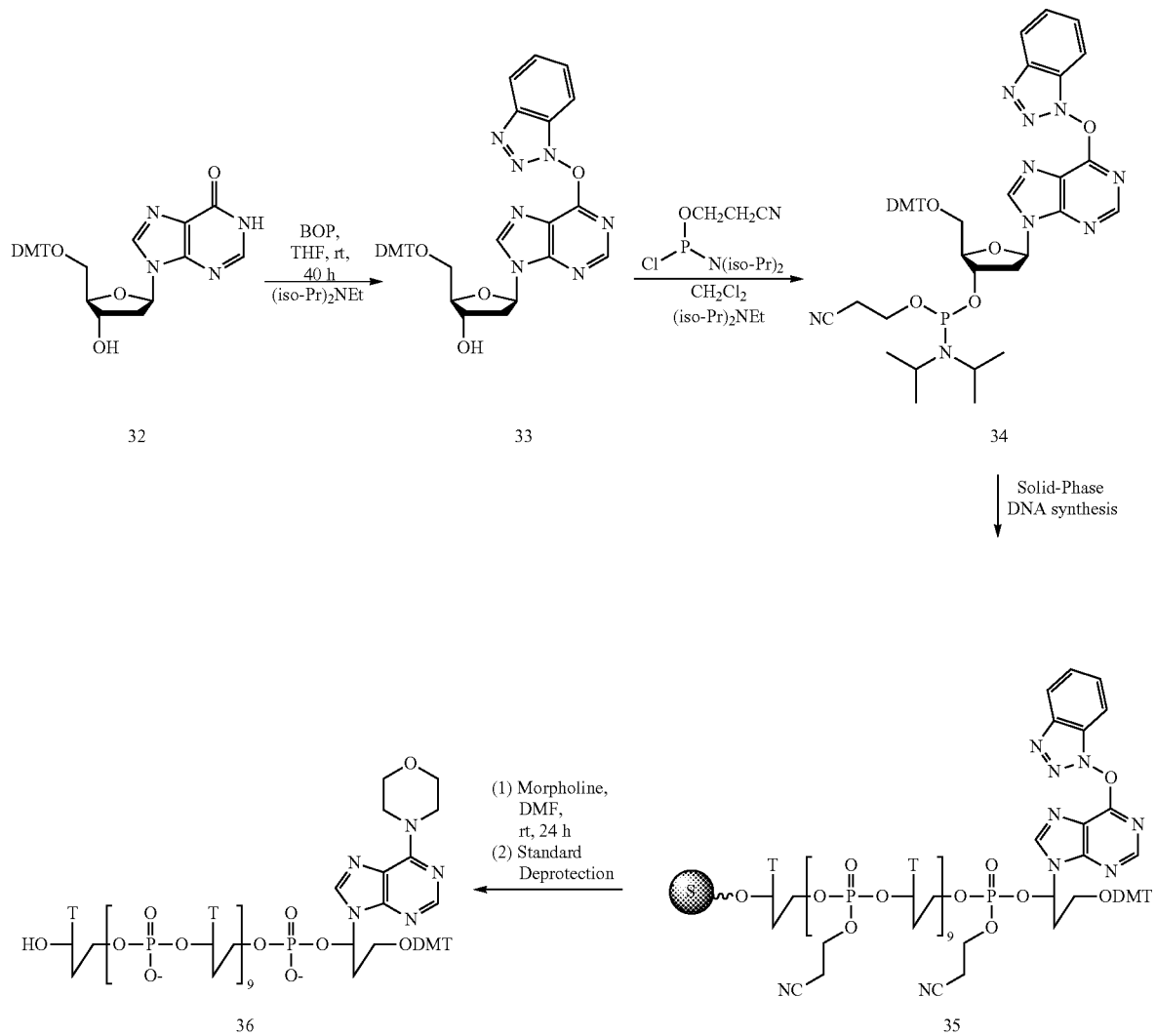

factors such as increased concentrations of compound 35 and longer coupling times. Only the desired morpholine modified oligomer 36 was obtained by the reaction. The ammonia displacement product was not observed. The ammonia displacement product would have been formed in the ammonia cleavage step had incomplete displacement by morpholine occurred. Accordingly, the DNA containing the reactive nucleoside underwent conversion in essentially quantitative yield to compound 35. The results from these experiments indicate the suitability of phorphoramidite 34 for DNA incorporation and for displacement reactions post-assembly.

Example 37

Synthesis of 1,$N^6$-ethano- and 1,$N^6$-propano-2'-deoxyadenosine analogues

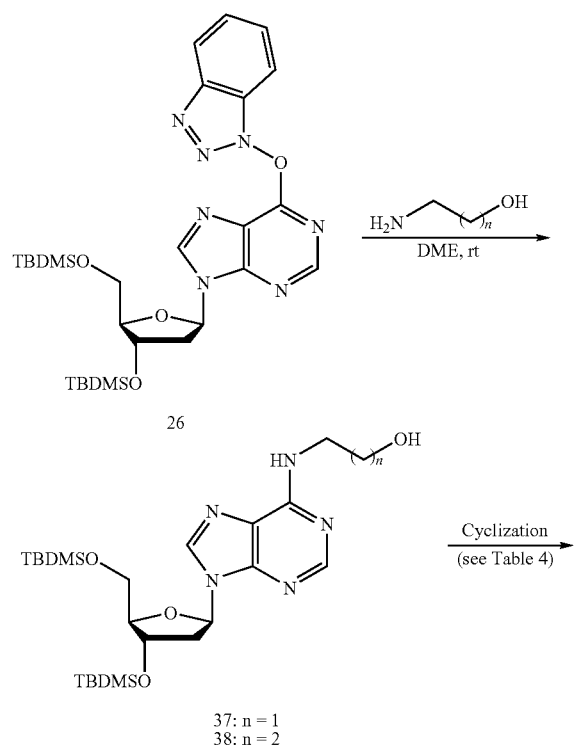

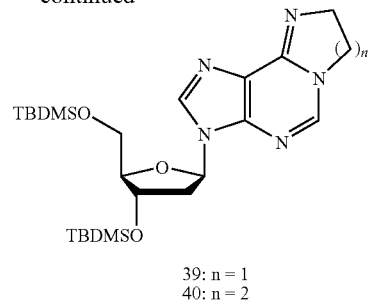

39: n = 1
40: n = 2

In reaction scheme above, compound 26 is a precursor to 1,$N^6$-ethano-2'-deoxyadenosine and 1,$N^6$-propano-2'-deoxyadenosine. The synthetic methodology is adequately flexible to accommodate chain length variation.

The $O^6$-(benzotriazol-1-yl)inosine nucleosides undergo reactions with both alcohols and amines, however, the former requires the use of $Cs_2CO_3$. Using this difference in reactivity, compound 26 was allowed to react with either 2-aminoethanol or with 3-amino-1-propanol in 1,2-dimethoxyethane (DME) at room temperature. The amination products 37 and 38 were obtained in 95% and 96% yields, respectively. Conversion of the terminal hydroxyl group in 37 and 38 to an iodide resulted in spontaneous cyclization to 39 and 40. For this cyclization two methods were evaluated; $(PhO)_3P^{30}MeI^-/Et_3N$ in DMF and $PPh_3/I_2/DIPEA/CH_2Cl_2$. The results from these experiments are shown in Table 4. Both sets of reagents produced the desired cyclization in reasonable, but slightly differing yields.

TABLE 4

| | Conditions tested for the cyclization of 6 and 7 | | |
|---|---|---|---|
| Entry | Substrate | Cyclization conditions | Product, yield[a] |
| 1 | 37, n = 1 | $(PhO)_3P^+MeI^-$, $Et_3N$, DMF, rt, 3 h | 39, 51% |
| 2 | 37, n = 1 | $PPh_3$, $I_2$, DIPEA, $CH_2Cl_2$, 8 h | 39, 61% |
| 3 | 38, n = 2 | $(PhO)_3P^+MeI^-$, $Et_3N$, DMF, rt, 3 h | 40, 78% |
| 4 | 38, n = 2 | $PPh_3$, $I_2$, DIPEA, $CH_2Cl_2$, 8 h | 40, 62% |

[a]Yield of isolated and purified product.

INCORPORATION OF SEQUENCE LISTING

Incorporated herein by reference in its entirety is the Sequence Listing for the application. The Sequence Listing is disclosed on a computer-readable ASCII text file titled, "Sequence Listing", created on Nov. 20, 2012. The Sequence Listing.txt file is 1 kb in size.

We claim:
1. A compound having the formula ZOR, wherein:
Z represents:

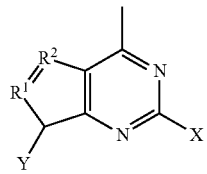

R represents:

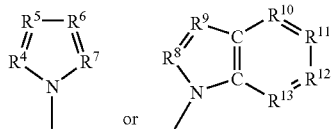

$R^1$ and $R^2$ independently represent $CR^3$ or N;
$R^4$, $R^5$, $R^6$, $R^7$, $R^8$, $R^9$, $R^{10}$, $R^{11}$, $R^{12}$, and $R^{13}$ represent, independently, N or CQ, with the proviso that no more than three of $R^4$, $R^5$, $R^6$, and $R^7$ represents N;
X represents $R^{14}$, —$OR^{15}$, $SR^{15}$, —$N(R^{14})_2$, $R^{14}C(O)$—, nitro, or halo;
Q and $R^3$, independently of each other, and independently at each position, represent $R^{14}$, —$OR^{15}$, —$SR^{15}$, —$N(R^{14})_2$, $R^{14}C(O)$—, nitro, or halo;
Y represents $R^{14}$ or a saccharide moiety;
$R^{14}$ independently represents H, an alkyl group, a carbocyclic aryl group, or a heterocyclic group; and
$R^{15}$ independently represents $R^{14}$ or a protecting group; wherein:
  alkyl groups are branched or unbranched and have 1-18 carbon atoms;
  alkyl groups are optionally substituted with halo groups;
  carbocyclic aryl groups have a total of 6-20 carbon atoms, including carbon atoms of substituents;
  heterocyclic aryl groups have a total of 5-20 carbon atoms, including carbon atoms of substituents; and
  carbocyclic aryl groups and heterocyclic aryl groups are unsubstituted, or optionally substituted at any position with one or more of $R^{14}$, —$OR^{15}$, —$SR^{15}$, —$N(R^{14})_2$, $R^{14}C(O)$—, nitro, or halo.

2. A compound according to claim 1, wherein Y represents a saccharide moiety, and the saccharide moiety has the following structure:

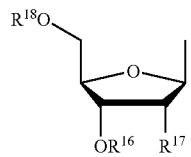

wherein:
$R^{16}$ represents H or a protecting group;
$R^{17}$ represents H or $OR^{16}$; and
$R^{18}$ represents $R^{15}$.

3. A compound according to claim 2, wherein $R^{18}$ represents an alkyl group or $R^{16}$.

4. A compound according to claim 3, wherein $R^{18}$ represents an alkyl group selected from the group consisting of methyl and ethyl.

5. A compound according to claim 2, wherein $R^{18}$ represents $R^{16}$.

6. A compound according to claim 1, wherein R represents:

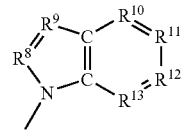

7. A compound according to claim 6, wherein no more than one of $R^{10}$, $R^{11}$, $R^{12}$, and $R^{13}$ represent N.

8. A compound according to claim 7, wherein $R^8$, $R^9$, and $R^{13}$ represent N.

9. A compound according to claim 1, wherein:
$R^1$ represents CH;
$R^2$ represents N;
X represents H; and
Y represents a saccharide moiety.

10. A compound according to claim 9, wherein the saccharide moiety is a 1-ribosyl or 2-deoxy-1-ribosyl.

11. A compound according to claim 1, wherein R represents:

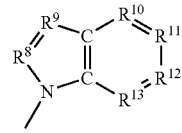

$R^8$ and $R^9$ represent N; and
$R^{10}$, $R^{11}$, $R^{12}$, and $R^{13}$ represent CH.

12. A compound according to claim 1, wherein

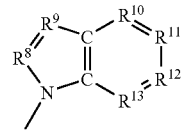

R represents:
$R^1$ represents CH;
$R^2$, $R^8$, and $R^9$ represent N;
$R^{11}$, $R^{12}$, and $R^{13}$ represent CQ;
Q and X represent H; and Y represents a saccharide moiety, wherein the saccharide moiety has the following structure:

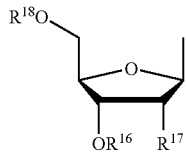

wherein:
$R^{16}$ represents H or a protecting group;
$R^{17}$ represents H or $OR^{16}$; and
$R^{18}$ represents $R^{15}$.

13. A compound according to claim 12, wherein $R^{18}$ is represented by $R^{16}$.

14. A compound according to claim 12, wherein $R^{18}$ is represented by an alkyl group, wherein the alkyl group is methyl or ethyl.

15. A compound having the formula ZOR, wherein:
Z represents:

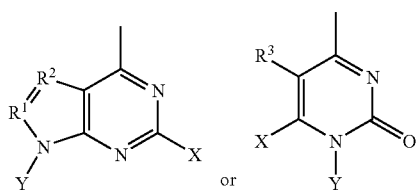

R represents:

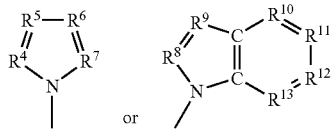

$R^1$ and $R^2$ independently represent $CR^3$ or N;
$R^4$, $R^5$, $R^6$, $R^7$, $R^8$, $R^9$, $R^{10}$, $R^{11}$, $R^{12}$, and $R^{13}$ represent, independently, N or CQ, with the proviso that no more than three of $R^4$, $R^5$, $R^6$, $R^7$ represents N;
X represents $R^{14}$, —$OR^{15}$, $SR^{15}$, —$N(R^{14})_2$, $R^{14}C(O)$—, nitro, or halo;
Q and $R^3$, independently of each other, and independently at each position, represent $R^{14}$, —$OR^{15}$, —$SR^{15}$, —$N(R^{14})_2$, $R^{14}C(O)$—, nitro, or halo;
Y represents a saccharide moiety having the following structure:

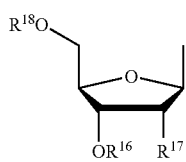

$R^{14}$ independently represents H, an alkyl group, a carbocyclic aryl group, or a heterocyclic aryl group;
$R^{15}$ independently represents $R^{14}$ or a protecting group;

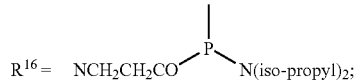

$R^{17}$ is hydrogen; and
$R^{18}$ is a protecting group;
wherein:
alkyl groups are branched or unbranched and have 1-18 carbon atoms;
alkyl groups are optionally substituted with halo groups;
carbocyclic aryl groups have a total of 6-20 carbon atoms, including carbon atoms of substituents;
heterocyclic aryl groups have a total of 5-20 carbon atoms, including carbon atoms of substituents; and
carbocyclic aryl groups and heterocyclic aryl groups are unsubstituted, or optionally substituted with one or more of $R^{14}$, —$OR^{15}$, —$SR^{15}$, —$N(R^{14})_2$, $R^{14}C(O)$—, nitro, or halo.

16. A compound having the formula Z—O—R-$(L)_n$-Po, wherein:
Z represents:

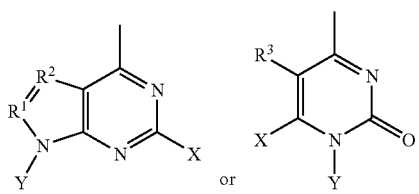

R represents:

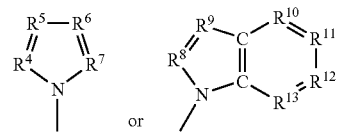

$R^1$ and $R^2$ independently represent $CR^3$ or N;
$R^4$, $R^5$, $R^6$, $R^7$, $R^8$, $R^9$, $R^{10}$, $R^{11}$, $R^{12}$, and $R^{13}$ represent, independently, N or CQ, with the proviso that no more than three of $R^4$, $R^5$, $R^6$, $R^7$ represents N;
X represents $R^{14}$, —$OR^{15}$, $SR^{15}$, —$N(R^{14})_2$, $R^{14}C(O)$—, nitro, or halo;
Q and $R^3$, independently of each other, and independently at each position, represent $R^{14}$, —$OR^{15}$, —$SR^{15}$, —$N(R^{14})_2$, $R^{14}C(O)$—, nitro, or halo;
Y represents $R^{14}$ or a saccharide moiety;
$R^{14}$ independently represents H, an alkyl group, a carbocyclic aryl group, or a heterocyclic aryl group;
$R^{15}$ independently represents $R^{14}$ or a protecting group;
wherein:
alkyl groups are branched or unbranched and have 1-18 carbon atoms;
alkyl groups are optionally substituted with halo groups;

carbocyclic aryl groups have a total of 6-20 carbon atoms, including carbon atoms of substituents;
heterocyclic aryl groups have a total of 5-20 carbon atoms, including carbon atoms of substituents;
carbocyclic aryl groups and heterocyclic aryl groups are unsubstituted, or optionally substituted with one or more of $R^{14}$, —$OR^{15}$, —$SR^{15}$, —$N(R^{14})_2$, $R^{14}C(O)$—, nitro, or halo;

L represents any chain of up to 20 atoms selected from the group consisting of carbon, nitrogen, oxygen, and sulfur moieties wherein:
the carbon moiety is —$CH_2$—, —C(O)—, or phenyl;
the nitrogen moiety is —$N(R^{14})$—,
the oxygen moiety is —O—,
the sulfur moiety is —$S(O_2)$—;
with the proviso that when there is more than one oxygen moiety, at least two —$CH_2$— moieties are between the oxygen moieties; when there is more than one sulfur moiety, at least two —$CH_2$— moieties are between the sulfur moieties; where there is more than one —C(O)— moiety, at least one —$CH_2$— moiety is between the —C(O)— moieties; and not more than two nitrogen moieties are consecutive;

n is 0 or 1; and
Po represents an organic polymer, an inorganic polymer, or combinations thereof.

17. The compound according to claim 16 wherein L is represented by -$(A^1)_a$-$(A^2)_b$-$(A^3)_c$-$(Ph)_k$-, wherein:
$A^1$, $A^2$, and $A^3$ independently represent —$CH_2$—, —C(O)—, —O—, —$N(R^{14})$—, or —$S(O_2)$—;
each $A^1$, $A^2$, and $A^3$ is different from the other two;
Ph represents phenyl;
a, b, and c are independently 0, 1, or 2; and
k is 0 or 1.

18. The compound according to claim 17 wherein at least one of a, b, and c is not 0.

19. The compound according to claim 16 wherein L is represented by -$(A^1-A^2)_{m1}$-$(CH_2)_{m2}$-$(Ph)_k$-Po, wherein:
$A^1$ and $A^2$ independently represent —C(O)—, —O—, —$N(R^{14})$—, or —$S(O_2)$—;
each $A^1$ and $A^2$ is different from the other;
Ph represents phenyl;
m1 and k are independently 0 or 1; and
m2 is 0, 1, or 2.

20. The compound according to claim 19 wherein at least one of m1 and m2 is not 0.

21. The compound according to claim 16 wherein the organic polymer is polyethylene glycol, polystyrene, or an amino resin.

22. The compound according to claim 16 wherein the inorganic polymer is glass beads, silica gel, alumina, controlled pore glass, or an amino-modified controlled pore glass.

23. A compound according to claim 16, having the following structure:

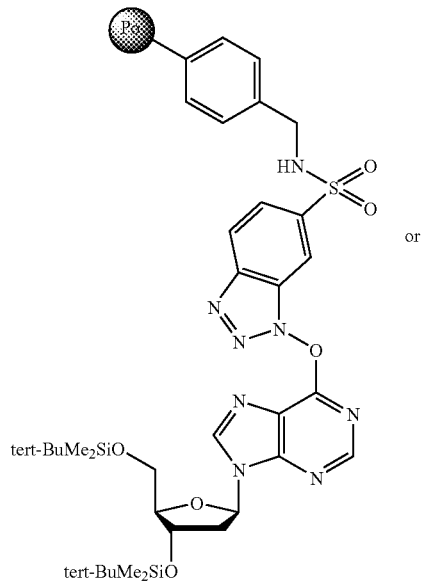

or

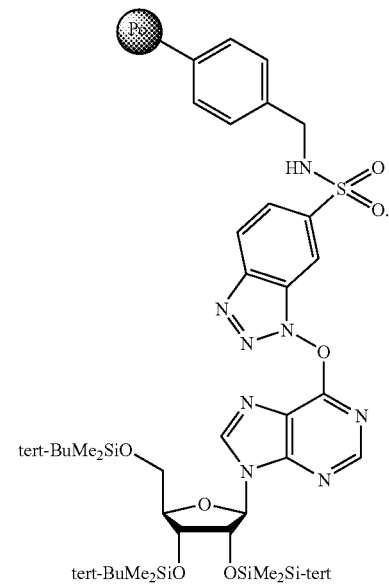

* * * * *

UNITED STATES PATENT AND TRADEMARK OFFICE
CERTIFICATE OF CORRECTION

PATENT NO.       : 8,501,931 B2                                           Page 1 of 1
APPLICATION NO.  : 12/444873
DATED            : August 6, 2013
INVENTOR(S)      : Lakshman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1151 days.

Signed and Sealed this
Fifteenth Day of September, 2015

Michelle K. Lee
*Director of the United States Patent and Trademark Office*

SEQUENCE LISTING

```
<160> NUMBER OF SEQ ID NOS: 1

<210> SEQ ID NO 1
<211> LENGTH: 11
<212> TYPE: DNA
<213> ORGANISM: Artificial Sequence
<220> FEATURE:
<223> OTHER INFORMATION: Synthetic nucleotide sequence
<220> FEATURE:
<221> NAME/KEY: misc_feature
<222> LOCATION: (11)..(11)
<223> OTHER INFORMATION: n is a terminal purine nucleoside with a
      morpholinyl group attached, and a dimethoxytrityl group is
      attached at the 5'-hydroxyl.
<400> SEQUENCE: 1
tttttttttt n                                                          11
```